United States Patent [19]
Demarest et al.

[11] Patent Number: 5,469,689
[45] Date of Patent: Nov. 28, 1995

[54] MACHINE FOR THE AUTOMATED PACKAGING OF NEEDLES AND ATTACHED SUTURES AND METHOD OF UTILIZING THE PACKAGING MACHINE

[75] Inventors: David Demarest, Parsippany; Robert B. Duncan, Bridgewater; Martin Sobel, Flemington, all of N.J.; Timothy P. Lenihan, Morrisville, Pa.; William Rattan, Cerritos, Calif.

[73] Assignee: Ethicon, Inc., Somerville, N.J.

[21] Appl. No.: 385,342

[22] Filed: Feb. 8, 1995

Related U.S. Application Data

[62] Division of Ser. No. 181,626, Jan. 13, 1994.

[51] Int. Cl.⁶ ................................................ B65B 63/04
[52] U.S. Cl. .................... 53/430; 53/415; 53/471; 53/475; 53/487; 53/488
[58] Field of Search ............................ 206/63.3; 53/116, 53/118, 131.3, 133.8, 135.1, 136.1, 147, 155, 156, 235, 237, 238, 247, 255, 267, 268, 281, 297, 329, 544, 411, 412, 415, 485, 487, 488, 429, 430, 443, 467, 445, 446, 473, 474, 475, 471

[56] References Cited

U.S. PATENT DOCUMENTS

| | | | |
|---|---|---|---|
| 2,746,118 | 3/1956 | Drummond et al. | 53/116 |
| 3,167,895 | 2/1965 | Egler et al. | 53/473 |
| 3,618,282 | 11/1971 | Hagel et al. | 53/116 X |
| 3,811,244 | 5/1974 | Killen et al. | 53/116 |
| 3,816,889 | 6/1974 | Crotti | 53/116 |
| 4,255,917 | 3/1981 | Stone | 53/116 X |
| 4,424,898 | 1/1984 | Thyen et al. | 206/63.3 |
| 4,922,904 | 5/1996 | Uetake et al. | 606/226 |
| 5,056,658 | 10/1991 | Sobel et al. | 206/63.3 |

Primary Examiner—John Sipos
Assistant Examiner—Daniel Moon
Attorney, Agent, or Firm—Scully, Scott Murphy & Presser

[57] ABSTRACT

An automated machine for the high-speed packaging of multiple surgical needles each with an attached suture into a tray and detachable cover structure providing a suture package utilized for the packaging of the needles and attached sutures. Additionally, the automated packaging machine incorporates operative mechanism adapted to wind the sutures into a peripheral channel of the tray and facilitating the attachment of the cover to the tray which contains the needles and attached wound sutures, and from which cover there is concurrently formed a separate product-identifying label as a component of the tray upon removal of the cover to gain access to the contents of the tray. The automated packaging machine also provides for a rotary turret or turntable for the high-speed sequential loading of successive forwardly indexed trays with the needles and attached sutures; the indexed advance of the needle and suture-filled tray to a suitable suture-winding station of the machine, the subsequent conveyance of the trays containing the needles and attached wound sutures to a cover-applying station of the machine to provide the suture packages, and the subsequent automated removal of the completed suture packages from the machine. Furthermore, the present invention is also directed to the provision of a novel method for the automated packaging of multiple surgical needles and attached sutures into trays and the application of covers thereto in sequential production steps through the intermediary of the automated packaging machine facilitating the high-speed output of suture packages containing multiple needles and attached sutures.

44 Claims, 18 Drawing Sheets

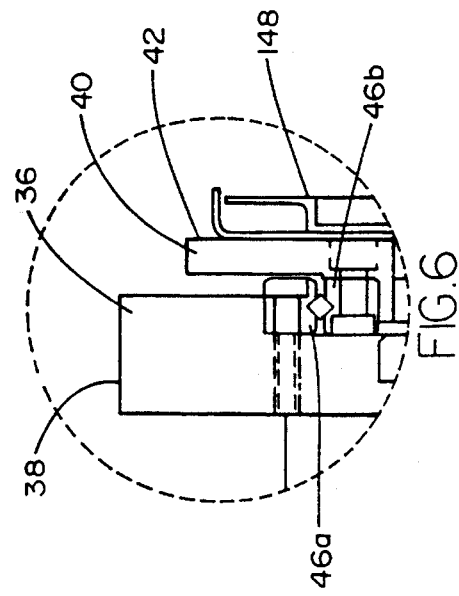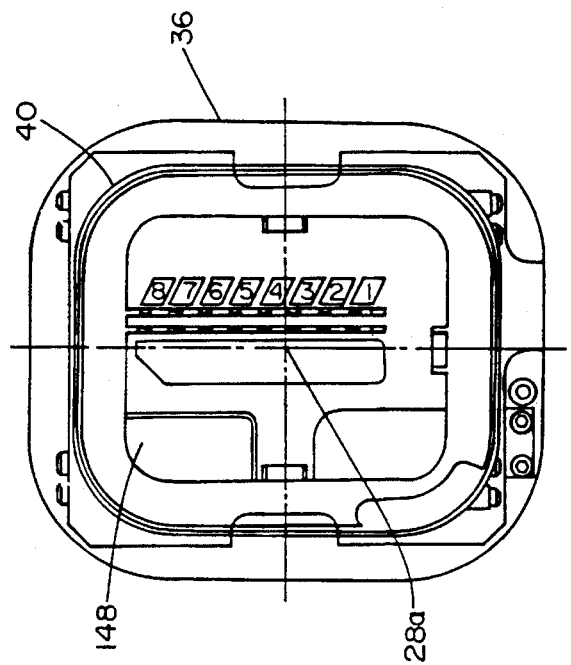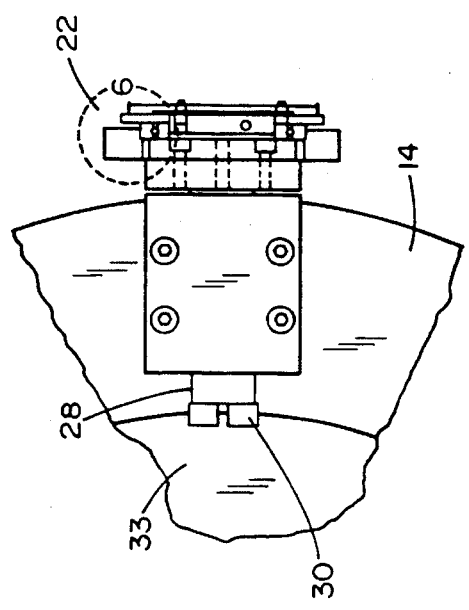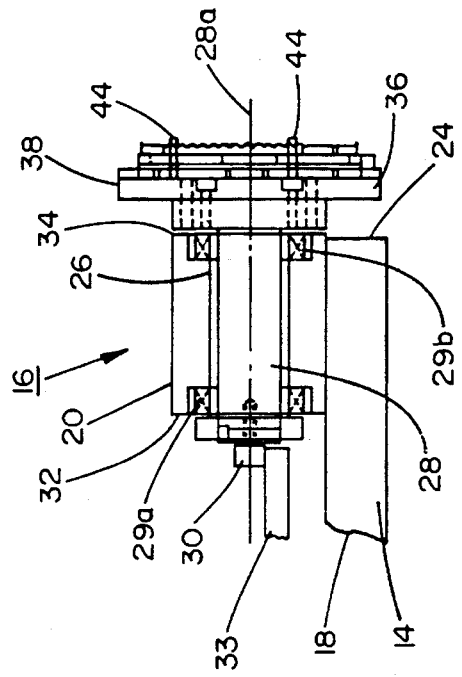

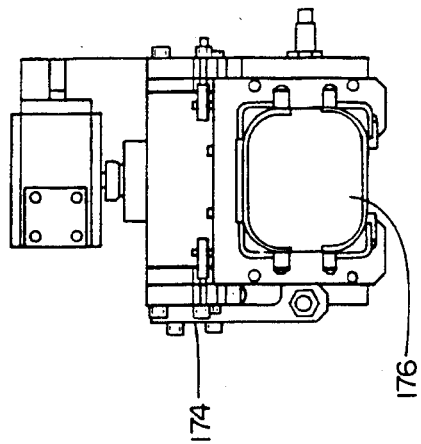
FIG.17
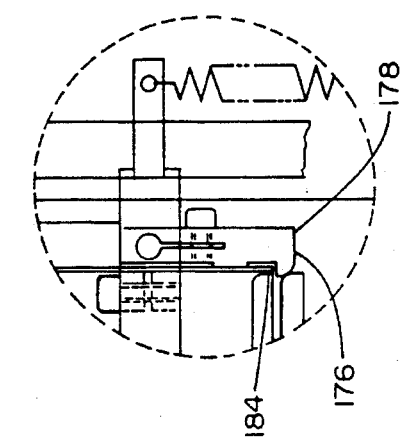
FIG.18
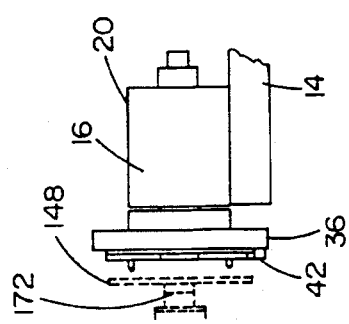
FIG.16
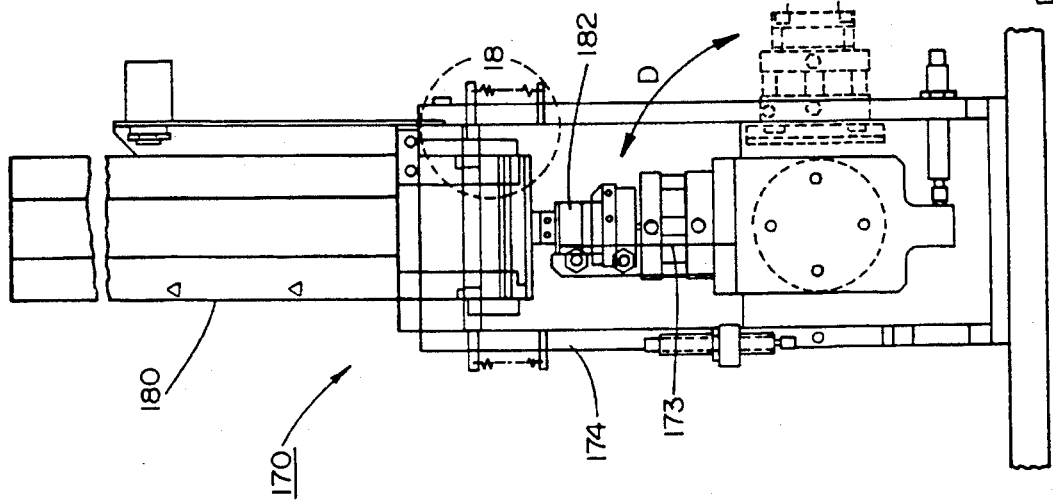

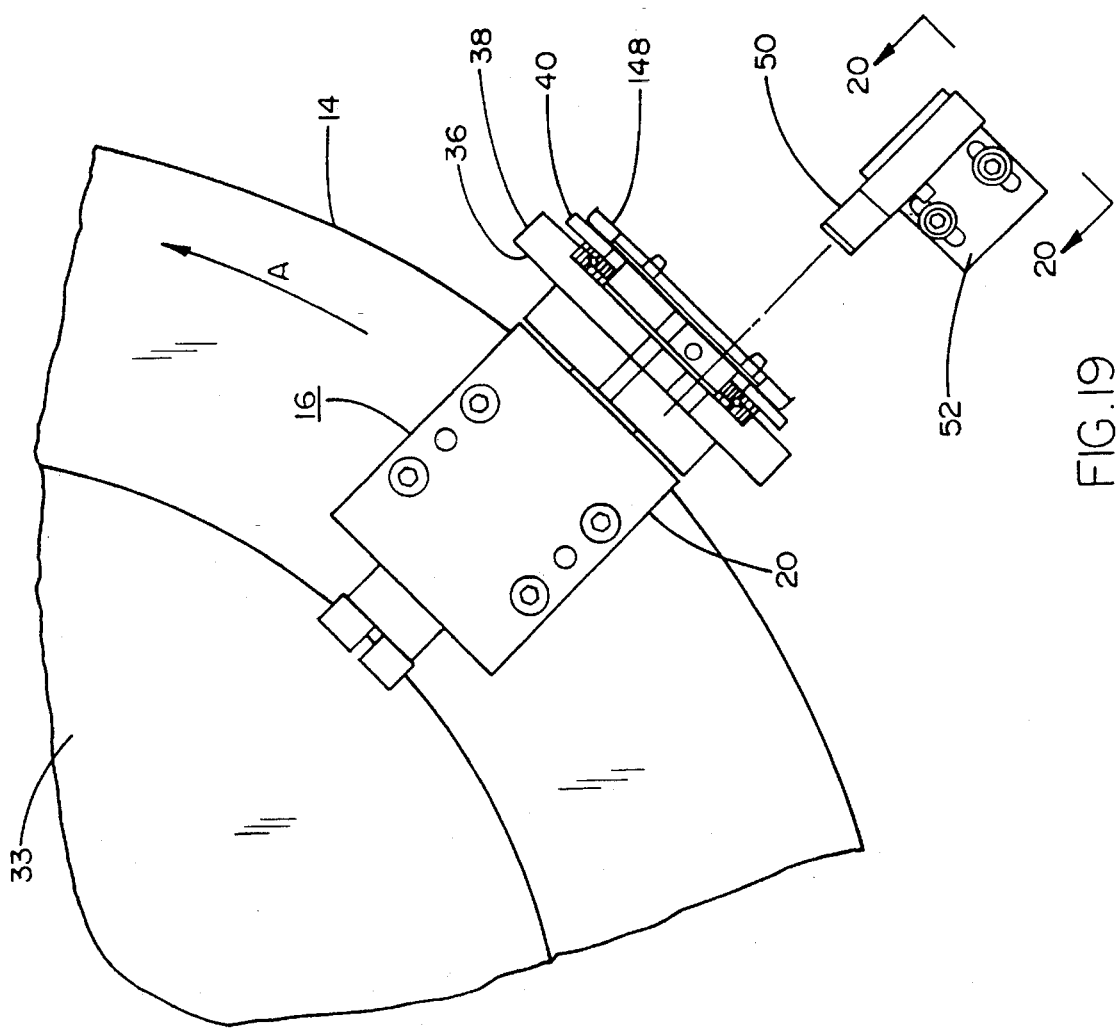

MACHINE FOR THE AUTOMATED PACKAGING OF NEEDLES AND ATTACHED SUTURES AND METHOD OF UTILIZING THE PACKAGING MACHINE

This is a divisional of application Ser. No. 08/181,626, filed on Jan. 13, 1994.

BACKGROUND OF THE INVENTION

1. Field of the Invention

The present invention relates to a machine for the automated packaging of surgical needles having sutures attached thereto and, more particularly, pertains to an automated machine for the high-speed packaging of multiple surgical needles each with an attached suture into a tray and detachable cover structure providing a suture package utilized for the packaging of the needles and attached sutures. Additionally, the automated packaging machine incorporates operative mechanism adapted to wind the sutures into a peripheral channel of the tray and facilitating the attachment of the cover to the tray which contains the needles and attached wound sutures, and from which cover there is concurrently formed a separate product-identifying label as a component of the tray upon removal of the cover to gain access to the contents of the tray.

The automated packaging machine also provides for a rotary turret or turntable for the high-speed sequential loading of successive forwardly indexed trays with the needles and attached sutures; the indexed advance of the needle and suture-filled tray to a suitable suture-winding station of the machine, the subsequent conveyance of the trays containing the needles and attached wound sutures to a cover-applying station of the machine to provide the suture packages, and the subsequent automated removal of the completed suture packages from the machine. The automated packaging machine is resultingly adapted to provide for the continuous and repetitive production of suture packages in a single high-speed production cycle without necessitating any manual manipulation thereof.

Furthermore, the present invention is also directed to the provision of a novel method for the automated packaging of multiple surgical needles and attached sutures into trays and the application of covers thereto in sequential production steps through the intermediary of the automated packaging machine.

Currently, in the medical, surgical and health-related technology, the high-speed and efficient packaging of either single or multiple sutures which are each suitably attached to surgical needles, such as by being swaged or similarly fastened thereto, in which such combined sets of needles and sutures are generally referred to as armed sutures, is imparted an increasing degree of importance in view of the rising demand of users for such combined surgical needles and attached sutures, and various diverse types of inexpensively manufactured suture packages for the containment of needles and attached sutures have been developed and are presently widely employed.

In specific instances, suture packages may be covered tray-shaped containers designed to receive and fixedly retain therein a plurality of needles and therewith attached sutures, in which the suture packages, upon opening of the covers, must enable the uncomplicated and simple withdrawal of individual needles and their attached sutures in a smooth unobstructed manner. In essence, when the needle which is to be removed from the suture package is engaged by a surgeon or health professional, for example, by being gripped through the intermediary of a forceps and then pulled out of the suture tray, it is essential that the needle easily disengage from its restraint in the package while the suture which is attached to the needle should also be readily able to slip out of the tray in the absence of any binding or snagging, and also without becoming entangled with other sutures still remaining in the suture tray or package. Thus, pursuant to a specific needle and suture package construction which, for example, may comprise an injection-molded plastic tray, the needles are generally engaged by clamping structure located in the tray so as to be "parked" or retained in predetermined array in a central region of the tray. The sutures extending from the needles to which they are attached are then conducted into and deposited in a peripheral channel formed about the suture tray so as to extend along the peripheral length of the channel. This positioning of the needles, and particularly that of the sutures within the peripheral channel of the tray is intended to eliminate tight bends or curves normally imposed on the sutures so as to facilitate their easy individual withdrawal from the suture package while eliminating any potential entanglement with the remaining sutures or snagging on the structure of the tray or package.

In connection with the foregoing, a generally flat, tray-shaped suture package of this type has been recently developed in the technology and which provides for the storage therein of multiple surgical needles and attached sutures, while concurrently recognizing the need to facilitate the smooth and unobstructed withdrawal of individual needles and attached sutures from the suture package. For instance, such a suture package is disclosed in a copending U.S. patent application Ser. No. 07/901,356 entitled "Multi-Strand Suture Package and Cover-Latching", which was issued Jul. 27, 1993 as U.S. Pat. No. 5,230,424, and which is commonly assigned to the assignee of the present application; and wherein the suture package is referred to as an RSO package (Reduced Size Organizer).

In the specific design of the flat tray-shaped plastic container having a peripheral channel as disclosed in the above-mentioned copending patent application, the suture package is basically constituted of a rectangular round-cornered and flat-bottomed injection-molded plastic tray having a flat central surface area including a raised needle clamping structure formed thereon for engaging and "parking" a plurality of needles in a predetermined spaced array. Sutures each have one end thereof attached to each of the respective needles so as to form so-called "armed sutures". The sutures extend from each of the needles into a channel extending about the perimeter or periphery of the suture tray and are conducted into the channel so as to be essentially wound within the circumferential confines of the suture tray. The plurality of sutures which are positioned within the suture tray channel are protected against inadvertent outward displacement therefrom through the presence of a multiplicity of contiguously positioned resilient fingers which are integrally molded with the suture tray, and which project outwardly above the confines of the channel along a major portion of the length of the channel and, collectively, form a so-called "zipper structure" in which the inherently resilient nature of the fingers facilitates their temporary raising up to enable the introduction of the sutures into the suture tray channel by means of a suitable suture winding apparatus.

2. Discussion of the Prior Art

At the present time, the introduction of needles with attached sutures into suture packages or molded plastic trays is being implemented in a substantially manual manner. In that instance, the needles are manually placed into the tray so as to be clampingly engaged by means of suitable needle-gripping structure, and thereafter the attached sutures are wound or positioned within the confines of the tray. Subsequently, a suitable cover is superimposed upon and fastened to the filled tray, and the resultant suture package conveyed to a suitable arrangement for possible sterilizing or further overwrapping.

The foregoing essentially manual and relatively basic process for winding the sutures into the tray, and especially the locating thereof into the peripheral channel of the tray during manipulation of the tray, is quite time-consuming, and in conjunction with the manual application of the cover into the tray in a basically individual or piece-by-piece mode, represents a serious hindrance to a large volume or mass produced manufacturing output, and adversely affects the economics in attempting to provide such large quantities of suture packages containing multiple surgical needles and attached sutures.

More recently, there has been developed a generally semi-automated winder machine for packaging surgical needles and attached sutures in a tray-like suture package, and which is the subject matter of a copending patent application entitled "Suture Winder Machine", commonly assigned to the assignee of the present application, and wherein at least some of the previously manually implemented packaging steps have been automated in order to be able to increase the output of needle and suture-containing packages while simultaneously reducing the number of manual procedures in effectuating the packaging of those particular items.

To that effect, the semi-automated winder machine, although necessitating the manual orientation of the trays for implementing the filling thereof with needles and attached sutures, includes a winding station which will to a considerable degree automate the winding process for the sutures so as to place the latter into a peripheral channel extending about the circumference of the tray. Also provided is a further therewith operatively associated device which will enable covers manually placed on the needle and suture-filled trays to be fastened thereto by means of a pressing die forming latchingly engaging interconnections between each of the covers and the trays, while concurrently producing from a portion of the cover a product-identifying label which remains permanently attached to the tray upon subsequent detachment of the cover. Although providing a considerable advance over the current state-of-the-art in the packaging of needles and sutures, the semi-automated winder machine as discussed hereinabove nevertheless necessitates the implementation of a considerable number of manual and labor-intensive handling steps in effectuating the filling of the trays with surgical needles and attached sutures, attaching the cover and, generally, producing complete suture packages.

SUMMARY OF THE INVENTION

Accordingly, the present invention unambiguously and in a significant manner improves upon the foregoing semi-automated needle and suture package-forming concept through the provision of a novel and unique substantially fully automated packaging machine adapted to, in a highly efficient and extremely rapid mode, continually fill successive trays of the type described hereinabove with surgical needles and attached sutures, subsequently causing the sutures to be wound into the confines of the tray, such as into a peripheral channel extending about the tray. Thereafter, the packaging machine is designed to implement the automated positioning and fastening of covers to the needle and suture-filled trays to produce completed suture packages of the type described hereinabove, which are adapted to be transported to a suitable locale for either further processing, such as sterilizing, and/or overwrapping, as is required by this technology.

In order to attain the foregoing essentially automated packaging of surgical needles with attached sutures, the automated packaging machine pursuant to the invention contemplates the provision of a rotary turret or turntable having a plurality of tool nests including suture tray supporting surfaces circumferentially spaced so as to be distributed about the periphery thereof. The rotary turret is rotated to cause the tool nests supporting the trays to be indexed forwardly so as to advance among a plurality of successive workstations which are adapted to, respectively, effectuate the supplying of each of the trays located on the tool nests or support surfaces with a specified quantity of surgical needles and attached sutures, winding the sutures into the confines of each needle and suture-filled tray and forming latching structures between the cover and the tray and producing a product-identifying label from a cover portion separated from the remaining cover, which separated portion is adapted to remain permanently attached to the tray upon subsequent detaching of the cover, and thereafter conveying each completed suture package to a suitable locale for further processing, overwrapping or other disposition thereof.

Operatively communicating in synchronism with the indexing rotation of the rotary turret may be a device which is adapted to supply and automatically mount empty trays of the type described hereinabove on successive tool nests or support surfaces; or alternatively, the trays may be manually positioned thereon. Thereafter, each tray is successively indexed forwardly by the rotating turret to a workstation which will impart predetermined incremental displacing movement to the support surface and tray thereon essentially vertically perpendicular and somewhat angularly skewed relative to the plane of rotation of the rotary turret. This movement enables a feeding device including needle grippers to successively insert and position a specified number of surgical needles with attached sutures into the tray for latching engagement with needle-clamping structure formed in the tray so as to fasten the needles therein in a predetermined array, and with the sutures depending downwardly therefrom outwardly of the tray. The needle and suture-filled tray is then indexed forwardly to a successive workstation by rotation of the rotary turret, wherein a suture winding structure operatively cooperating with the tray and the tool nest supporting the tray imparts rotation of the tray about a central axis perpendicular to the tray plane and concurrently causes a stylus and camming device to wind the downwardly extending sutures into a peripheral tray channel extending about the tray. This particular workstation is also equipped with a vacuum-generating unit engaging the sutures so as to cause the sutures to be tensioned into bundled strands to facilitate the ready winding thereof into the channel of the suture tray.

Thereafter, the tool nest or support surface mounting the tray with the needles parked therein and the thereto attached sutures having been wound into the peripheral channel of the tray is indexed forwardly to a further workstation responsive to indexing rotation of the rotary turret; at which workstation operating mechanism applies a cover onto the tray and, concurrently, a pressing die imparts pressure to the cover to form latching structures in the cover which fasten the cover to the tray while simultaneously separating a portion of the cover to form a product-identifying label pressed into the tray and which remains permanently adhered to the tray upon a subsequent detaching of the cover when it is desired to gain access to the contents of the tray. Upon completion of this particular cover-attaching sequence, the resultingly formed complete suture package is indexed to a further workstation at which suitable grippers may engage the suture package or the latter manually gripped and the suture package is conveyed to a repository or receiving unit to be readied for further processing, such as sterilizing, overwrapping or the like, as required.

The foregoing sequence of operative steps is continually repeated for each successive tool nest on the rotary turret or turntable receiving an empty tray, while a preceding tool nest mounting a tray on the turret is undergoing the above-mentioned packaging cycle. Thus, a successive tray is always placed into a position of readiness at a preceding workstation and processed in a similar manner as before upon the following forward indexing advance of the rotary turret or turntable. This ensures a continuous packaging cycle for successive suture packages in a highly efficient and high-speed operation without the need for any or at most only minimal manual intervention in the operation of the packaging machine.

Intermediate the various workstations as set forth hereinbefore, there may optionally be arranged other workstations adapted to enable the ascertaining of the presence of empty trays at the initial workstation, for a verification of the proper number of needles having been inserted into the trays and for a visual inspection of the trays subsequent to the winding of the sutures into the tray channels.

Accordingly, it is a primary object of the present invention to provide a packaging machine facilitating the automated high-speed packaging of surgical needles having sutures attached thereto.

A more specific object of the present invention resides in the provision of a machine for the automated packaging of needles and attached sutures wherein the packaging is effected on a forwardly indexing rotary turret having a plurality of circumferentially spaced tray-supporting tool nests or support surfaces, and wherein empty trays positioned on the support surfaces are in succession equipped with specified quantities of needles and attached sutures; indexed to a workstation which includes operative mechanism facilitating the winding of the sutures into a peripheral channel extending about each tray; and then indexed to a further workstation in which a cover is applied onto and fastened to the tray by a pressing die so as to form a suture package containing a predetermined quantity of needles and attached sutures.

A more specific object of the present invention is to provide an automated machine for the packaging of surgical needles and attached sutures wherein the needles are automatically fed in succession and positioned in a predetermined spaced array in an empty suture tray which is mounted on a tool nest on a rotary indexing turret, the sutures being wound into the confines of a peripheral channel of the tray, and a cover fastened thereonto so as to form a needle and suture-containing package.

Yet another object of the present invention is to provide a machine for the automated packaging of a plurality of surgical needles and attached sutures in a manner as described herein, which also incorporates workstations enabling the inspection of the trays to verify the presence of the trays and contents thereof.

A still further object of the present invention is to provide a method for the automated packaging of surgical needles and attached sutures in suture packages, wherein a plurality of needles are inserted into a tray and clampingly fastened therein in a predetermined spaced array; the sutures being then bundled into strands and wound into a peripheral channel of the tray; and a cover being applied and fastened to the tray so as to latchingly engage the latter while simultaneously forming a product-identifying label from a separated portion of the cover which is permanently attached to the tray.

BRIEF DESCRIPTION OF THE DRAWINGS

Reference may now be had to the following detailed description of an exemplary embodiment of a machine for the automated packaging of surgical needles and attached sutures, as described hereinabove, taken in conjunction with the accompanying drawings; in which:

FIG. 3 illustrates, on an enlarged scale, a view similar to FIG. 2 showing one of the tool nests for mounting a needle and suture-receiving tray;

FIG. 4 illustrates, further enlarged, a front view of the tool nest of FIG. 3;

FIG. 5 illustrates a top plan view of the tool nest of FIG. 3;

FIG. 6 illustrates an enlarged fragmentary detail of the encircled portion in FIG. 3;

FIG. 16 illustrates an elevational side view of a suture package unloading arrangement in two operative conditions thereof;

FIG. 17 illustrates a view in the direction of the arrow 17—17 in FIG. 16;

FIG. 18 illustrates, on an enlarged scale a fragmentary view of the encircled portion in FIG. 16;

FIG. 19 illustrates, generally diagrammatically a package detector assembly operatively utilized in conjunction with the rotary turret as shown in FIG. 1;

FIG. 20 illustrates an elevational view of the detector assembly as viewed in the direction of line 20—20 in FIG. 19;

DETAILED DESCRIPTION OF A PREFERRED EMBODIMENT

Figure 1:
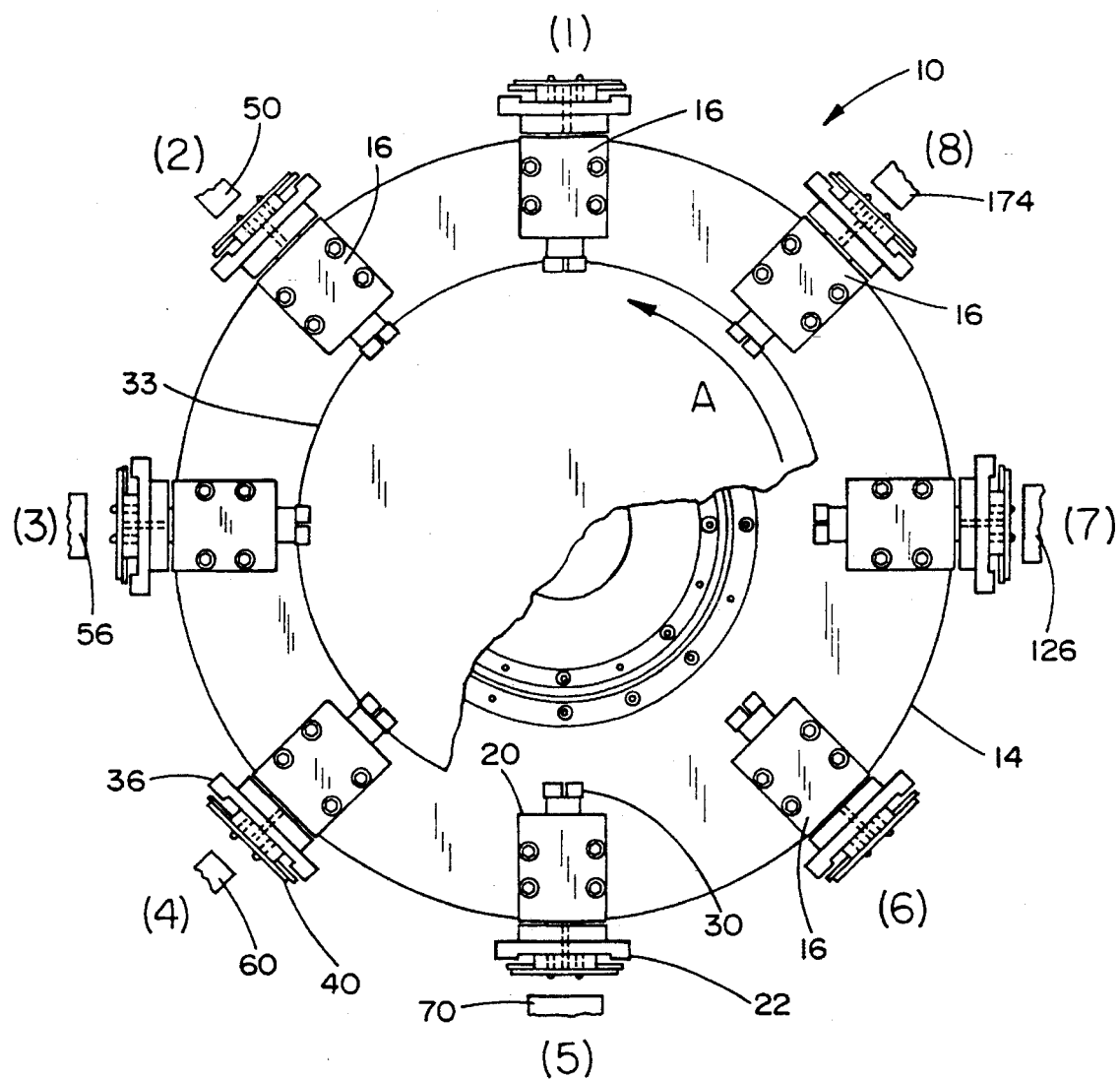
FIG. 1 illustrates a top plan view of the main rotary turret or turntable of the automatic packaging machine for needles and attached sutures.
Figure 2:
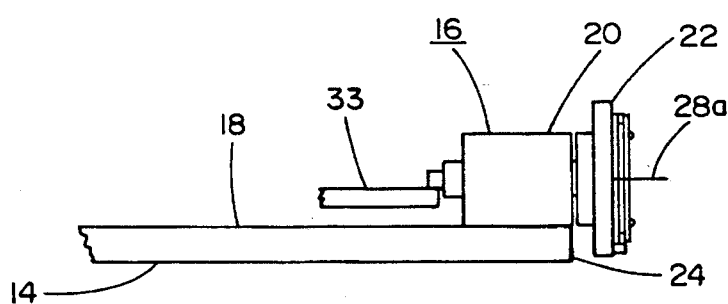
FIG. 2 illustrates a fragmentary side view of the rotary turret, showing a portion thereof incorporating one of the tray-mounting tool nests or support surfaces.

Referring now in more specific detail to the drawings, and particularly to FIGS. 1 through 6, FIG. 1 illustrates, generally diagrammatically, the rotary turret or turntable 10 which is essentially horizontally oriented so as to be rotatable through the intermediary of a program-controlled driving arrangement (not shown) about a vertical central axis, in this instance being rotatable in a counter-clockwise direction when viewed from above, as represented by arrow A.

The rotary turret 10 is essentially constituted of a circular disc-shaped member or dial 14 having a plurality of tool nests 16 located thereon in uniformly spaced circumferential array on the upper surface 18 of the dial 14 of rotary turret 10, and with each tool nest extending radially outwardly of the periphery thereof.

In this particular embodiment of the packaging machine, by way of example, there are provided eight tool nests 16 arranged at 45° angular spacings from each other about the circumference of the rotary turret 10. Each tool nest 16 consists of a housing 20, as shown in detail in FIGS. 3 through 6 of the drawings, which is fixedly mounted on the upper surface 18 of the disc-shaped rotary turret 14, and includes a portion 22 radially outwardly projecting from the circumferential edge 24 of the turret disc member 14, which is operative to receive and support flat-bottomed injection-molded plastic trays utilized in the forming of suture packages containing surgical needles and attached sutures, as described hereinbelow.

Figure 21:
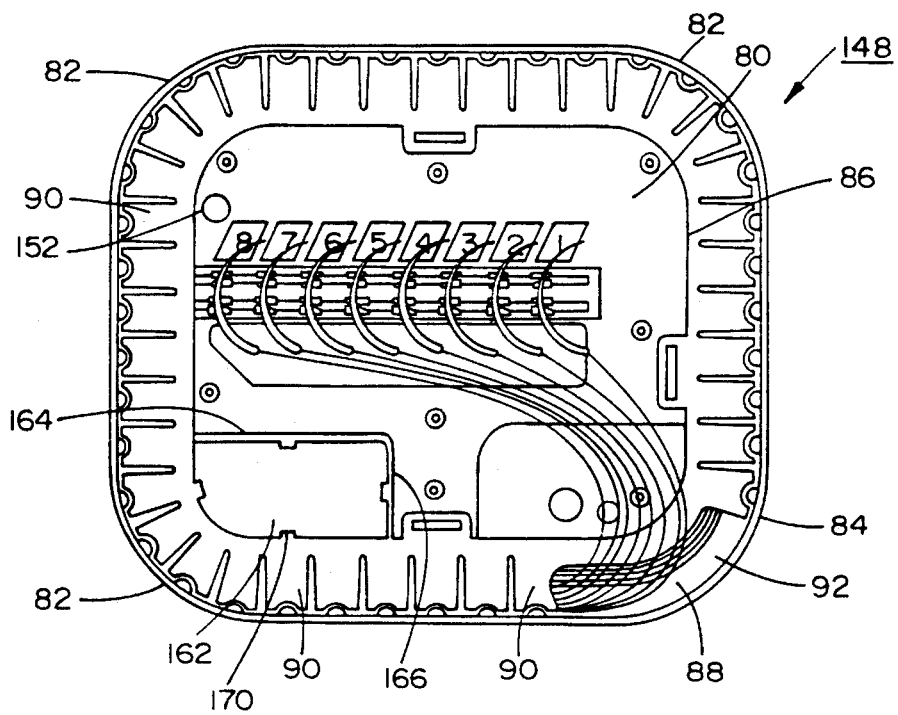
FIG. 21 illustrates a front view of a tray having needles and sutures arranged therein.
Figure 22:
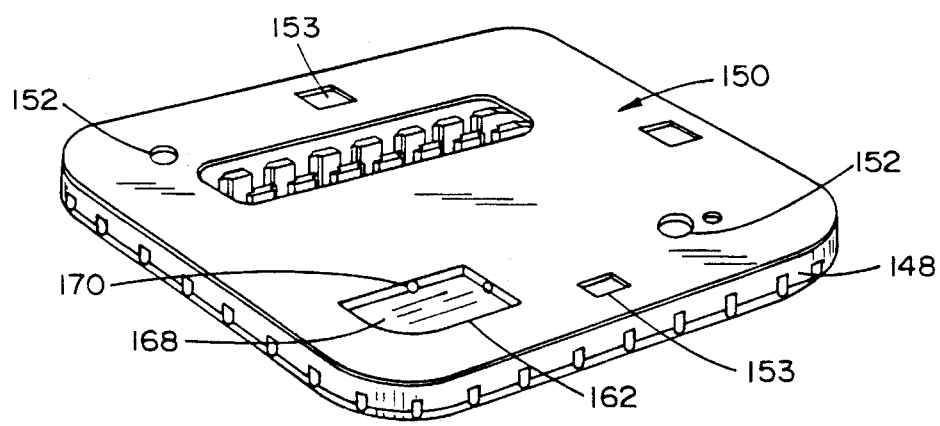
FIG. 22 illustrates a perspective view of a completed suture package.

As illustrated in drawing FIGS. 3 through 6, each of the tool nests 16 comprises a housing or block 20 fixedly mounted through suitable fasteners to the upper turret surface 18 proximate the peripheral outer rim or edge 24 of the rotary turret or dial 14. Each housing 20 includes a horizontal radially extending central bore 26 having a shaft 28 supported on bearings 29a and 29b rotatably journaled therein, with the shaft 28 being connectable to a suitable drive source, (as subsequently described). Cams 30 mounted on shaft 28 at the radially inner end 32 of the housing 20 are adapted to contact a stationary cam dial plate 33 extending over the dial surface 18, during the rotation of the rotary turret 10 for purposes as described in more specific detail hereinbelow in connection with the operation of tool nests 16. At the radially outer end 34 of the housing 20, there is provided structure for supporting the components for forming a suture package. The suture package initially comprises a generally flat injection-molded tray for receiving and retaining therein a plurality of surgical needles and attached sutures; for example, as illustrated in FIG. 21 of the drawings, and with an applied tray cover as shown in FIG. 22, as disclosed in a copending patent application Ser. No. 07/901, 356 entitled "Multi-Strand Suture Package and Cover-Latching", now U.S. Pat. No. 5,230,424 commonly assigned to the assignee of the present application; the disclosure of which is incorporated herein by reference.

The radially outer structure of the housing 20 for initially mounting the plastic suture tray includes a generally rectangular, round-cornered and vertically extending plate member 36 of which the outer peripheral surface 38 forms a cam surface, employed for a suture-winding purpose as described hereinbelow, and with the plate member 36 being secured to the radially outer end of the shaft 28 for rotation therewith. Mounted on the front surface of cam plate member 36 is a plate 40 having a radially outwardly facing, vertically-oriented support surface or platform 42 possessing projecting guide pins 44 for the registered positioning and mounting thereon of an injection-molded plastic tray adapted to be supplied with surgical needles and attached sutures. The cam plate member 36 and the plate 40 for supporting the suture tray are connected with each other so as to be secured against relative rotation, both being jointly rotatable about the longitudinal horizontal axis 28a of the shaft 28 extending through the block or housing 20. However, the plate 40 for mounting the tray is linearly displaceable relative to the cam plate member 36 through the interposition of cooperating slide guides 46 located between these elements. These slide guides 46 are disclosed in more extensive detail in the enlarged fragmentary illustration of FIG. 6, where they are illustrated as mating guide rails 46a and 46b, and are provided to facilitate the successive insertion of an array of surgical needles into the tray which is mounted on the guide pins 44 extending from the support surface 42 of the plate 40 on the tool nest 16.

The external configuration of both the cam plate member 36, i.e. its camming surface 38, and the support plate 40 is substantially in conformance with the outer shape of the suture tray, although larger in external dimensions than the latter.

In essence, the rotary turret or turntable 10 is adapted to be indexed forwardly in an angularly incremental rotational advance in the direction of arrow A in FIG. 1 such that each tool nest 16 supporting a suture tray is adapted to be advanced in succession to a number of workstations located stationarily spaced about the periphery of the rotary turret, as identified in FIG. 1 of the drawings.

The successive workstations which are utilized by the automated machine for packaging surgical needles and attached sutures are essentially as follows:

(1) A station designed to have an empty suture tray positioned on the radially outwardly facing platform or support surface 42 of the plate 40 on tool nest 16, and retained thereon by means of the guide pins 44 extending through positioning apertures in the tray so as to be in a generally vertical orientation relative to the horizontal plane of rotation of the rotary turret 10. Suitable grippers of a tray feeding apparatus or mechanism (not shown) may be provided to supply empty trays to successive plates 40 and position the trays thereon. The grippers may obtain an individual one of the trays from a suitable supply source, such as a stack of the trays, and position the trays one each on successive forwardly indexed platforms 42 of the tool nests 16. Alternatively, in the absence of gripper mechanisms the trays may optionally be manually positioned on the guide pins 44 of platform 42 such that the rear surface of each tray contacts the support surface or platform in a flat, surface-contacting relationship so as to be firmly mounted thereon.

(2) A package or tray-detecting workstation, as shown in FIGS. 19 and 20, which may be optional on the machine, includes a suitable sensor 50 which is mounted on the arm of a stationary bracket arrangement 52 to provide assurance that a tray has actually been physically positioned on the support surface or platform 42, and retained thereon by means of the guide pins 44 projecting radially outwardly through the apertures in the tray. The sensor 50 is adapted to provide this information to a control arrangement for the packaging machine as to the required presence of a tray in order to enable subsequent packaging steps to be implemented by the packaging machine responsive thereto.

(3) A subsequent workstation indexed in the direction of arrow A includes an operative needle-feeding mechanism 56, (as indicated in FIG. 1) for successively inserting a specified number of surgical needles and attached sutures into the suture tray which has been indexed forwardly by the rotary turret 10 so as to be located in front of needle-feeding mechanism 56. The structure and functioning of the needle-feeding mechanism 56 is elucidated in greater specificity in connection with the overall operation of the rotary turret 10 as set forth hereinbelow in conjunction with FIGS. 24 through 26c of the drawings. However, a more detailed description is also provided in copending patent application Ser. No. 08/181,598 assigned to the common assignee of the present application. The needles are fed by the mechanism 40 so as to be positioned on suitable clamping structure constituting an integral portion of the tray, such as raised components molded on the central bottom surface portion thereof, as shown in FIG. 21 of the drawings. Hereby, the plate 40 and its support platform 42 mounting the tray on the guide pins 44 is indexed incrementally vertically, such as in upwardly spaced steps, along a relative displacement between elements 46a and 46b of the slide guides 46, and resultingly between the cam plate member 36 and plate 40, to ensure that the appropriate number of needles are positioned therein by mechanism 50 at their intended arrayed locations in the tray. This needle feeding action is facilitated through the program-controlled vertical incremental displacement between the plate 40 having the tray-supporting platform 42 thereon and the cam plate member 36 by the relative sliding movement taking place therebetween. The surgical needles and attached sutures may be introduced into the tray through the intermediary of suitable grippers, as shown and described hereinbelow, engaging needles received from a suture attaching or swaging machine (not shown), and swinging the respective needle into its allotted position on the needle clamping or parking structure in the tray, whereupon the grippers are adapted to release the needle and retracted to engage and pick up a subsequent needle and attached suture for repeating the foregoing procedure until the desired quantity of needles and attached sutures has been parked in the tray.

Figure 7:
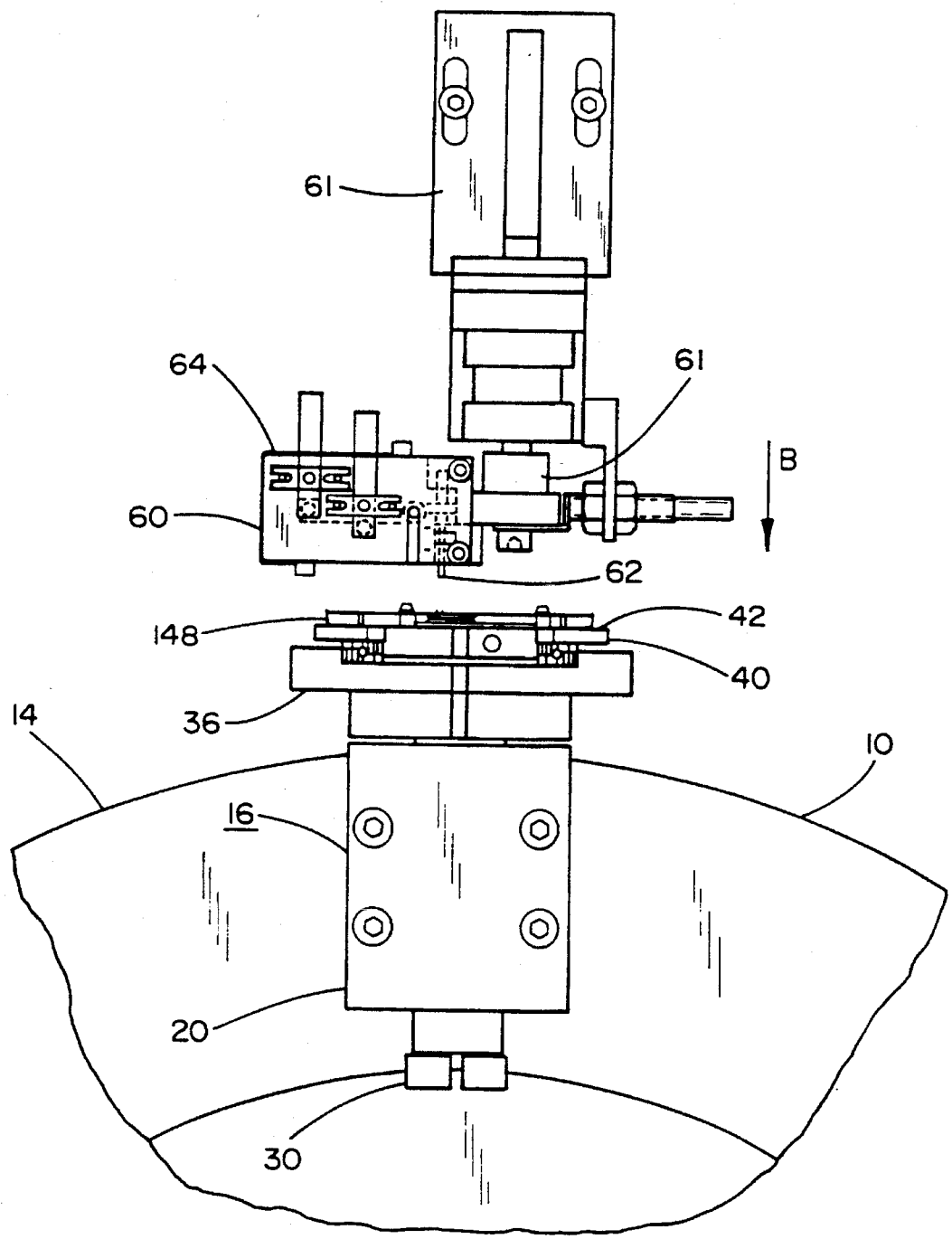
FIG. 7 illustrates a side view of a needle detector arrangement.

(4) At an optionally provided needle detector workstation there may be provided verification of the presence and proper positioning of the needles and sutures that were introduced into the tray by the needle-feeding mechanism 56 of FIG. 1 and FIGS. 24 through 26c. As is schematically illustrated in FIG. 7 of the drawings, a needle detector unit 60 consisting of a stationary bracket arrangement 61 is adapted to be positioned opposite the platform 42 which has been indexed in front thereof by the rotary turret 10, and mounting the needle-filled suture tray. A portion of the bracket arrangement 61 is then advanced axially towards the tray to enable a plurality of sensors 62 mounted on a housing 64 be movable along arrow B to ascertain and provide information that the appropriate number of surgical needles has been properly introduced into and parked in proper array in the tray by the needle-inserting or feed mechanism 56 of the preceding workstation. Upon the needle sensors 62 verifying to a control system for the machine the presence of the required quantity and parking of the surgical needles in the tray, the sensors 62 and housing 64 are retracted away from the tray on platform 42 to enable the rotary turret 10 to index the tool nest 16 forwardly to a further workstation.

(5) A suture winding workstation, to which the tray is adapted be indexed, comprises a suture winding apparatus 70, by means of which sutures depending from the needles outwardly of and hanging downwardly from the tray are wound into the confines of the tray, and particularly the peripheral channel as illustrated in FIG. 21, and as shown in FIGS. 8a, 8b, 8c and 9 of the drawings. The downwardly loosely hanging sutures extending from each of the needles, as described hereinbelow, are positionable so as to be tensioned in a stationary vacuum device or unit 72 located below the tool nest 16 supporting the suture tray at this workstation, and to thereby cause the sutures to be tensioned and bundled into a compact strand, the operational sequence of which is illustrated in and described in more extensive detail hereinbelow with regard to FIGS. 8a through 8c of the drawings directed to the operational aspects of winding apparatus 70.

The cam plate member 36 of the tool nest mounting the needle and suture-filled tray on platform 42 at this workstation is adapted to be contacted along the cam surface 38 thereof by cam follower components 74 located on a stylus arrangement 76 of apparatus 70, which is employed for guiding and winding the sutures into the peripheral channel of the tray. The stylus arrangement 76 includes a stationary cylinder 78 having a pneumatically-actuatable central piston 80 longitudinally reciprocable therein for movement towards and away from the tray. The cam follower components 74 comprise articulatingly connected rollers 74a and 74b contacting the peripheral cam surface 38 of the cam plate member 36, the latter of which, in conjunction with the support plate 40 mounting the tray, is rotated by the program-controlled rotation of shaft 28 about a horizontal central axis 28a extending normal to the plane of the plates 36, 40 and the tray so as to facilitate winding of the sutures into the peripheral channel of the tray, as shown and elucidated with regard to the description of operation of FIGS. 8a through 8c and 9.

Referring more specifically to the construction of the tray shown in FIG. 21 of the drawings, which as indicated hereinabove is essentially the needle and suture-containing tray constituting, in combination with an attached cover, the components of the multi-strand suture package of the above-mentioned U.S. Pat. No. 5,230,424. Referring to the basic constructional features thereof, the tray has a planar base 80 of generally rectangular configuration extending into rounded corners 82. Extending about the periphery of the base 80 is an upstanding wall 84, and spaced inwardly thereof in parallel relationship is a further upstanding wall 86 so as to form a peripheral channel structure 88 therebetween. Extending over the channel 88 outwardly from the inner wall 86 are a plurality of contiguously arranged essentially resilient retaining fingers 90, which are cantilevered so as to extend most of the way over the channel 88 from the upper edge of the inner wall thereof for preventing sutures from lifting up out of the channel. A gap 92 formed in the array of the retaining fingers 90 along the length of the channel, preferably proximate the juncture or corner between two of the rectangular sides of the tray permits the end of each of the sutures to emerge from the channel 88, as shown in FIG. 21 of the drawings.

The central region of the base 80 of the tray within the inner wall 86 includes integral structure which provides a plurality of spaced-apart gaps enabling the clamping therein of the suture needles so as to "park" the latter in the tray, as is clearly shown in the drawing, and with each of the needles having one end of a respectively associated suture attached or swaged thereto.

Figure 8A:
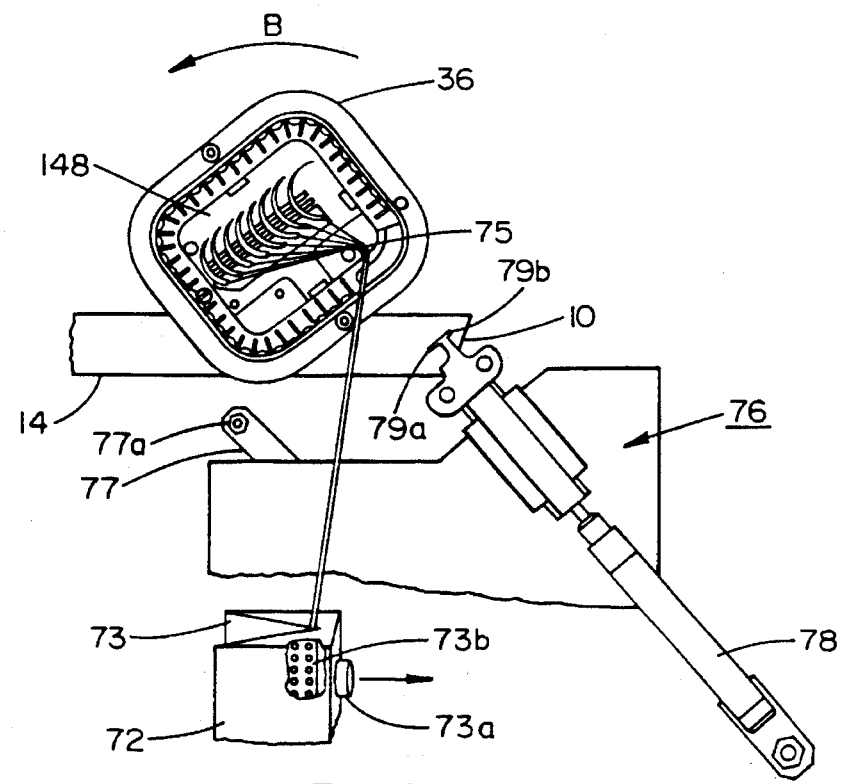
FIGS. 8a through 8c schematically illustrate, respectively, various stages in the operation of a winding arrangement for sutures.
Figure 8B:
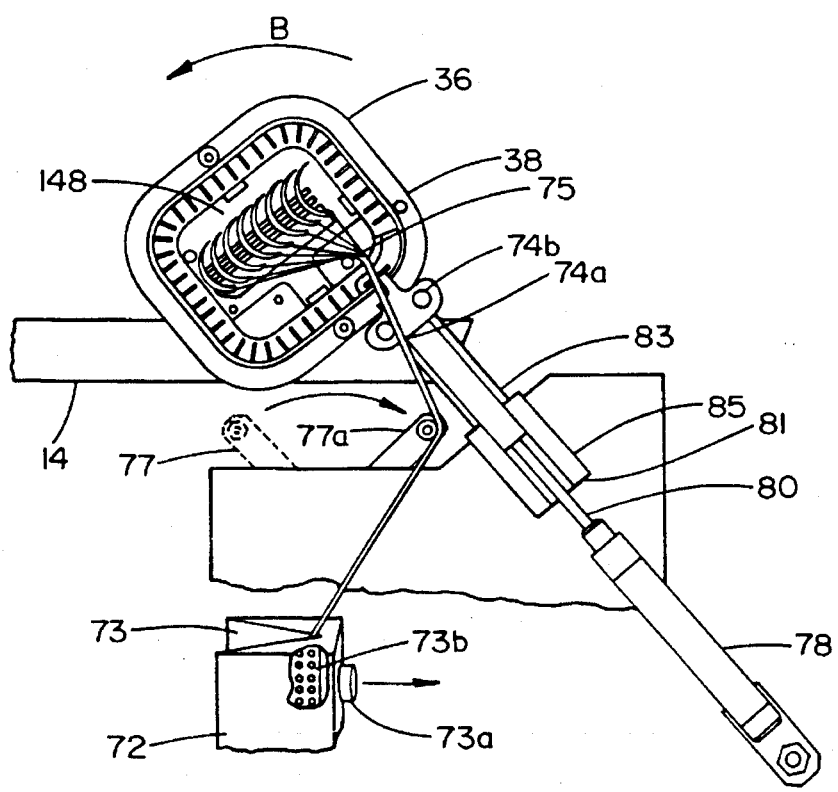
Figure 9:
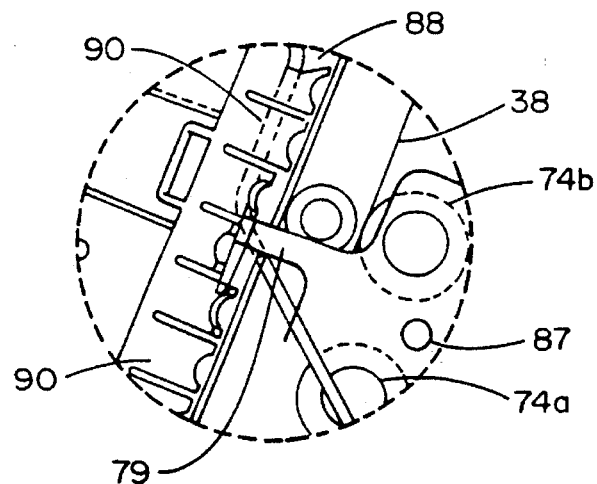
FIG. 9 is an enlarged fragmentary view of the encircled portion of FIG. 8c.
Figure 8C:
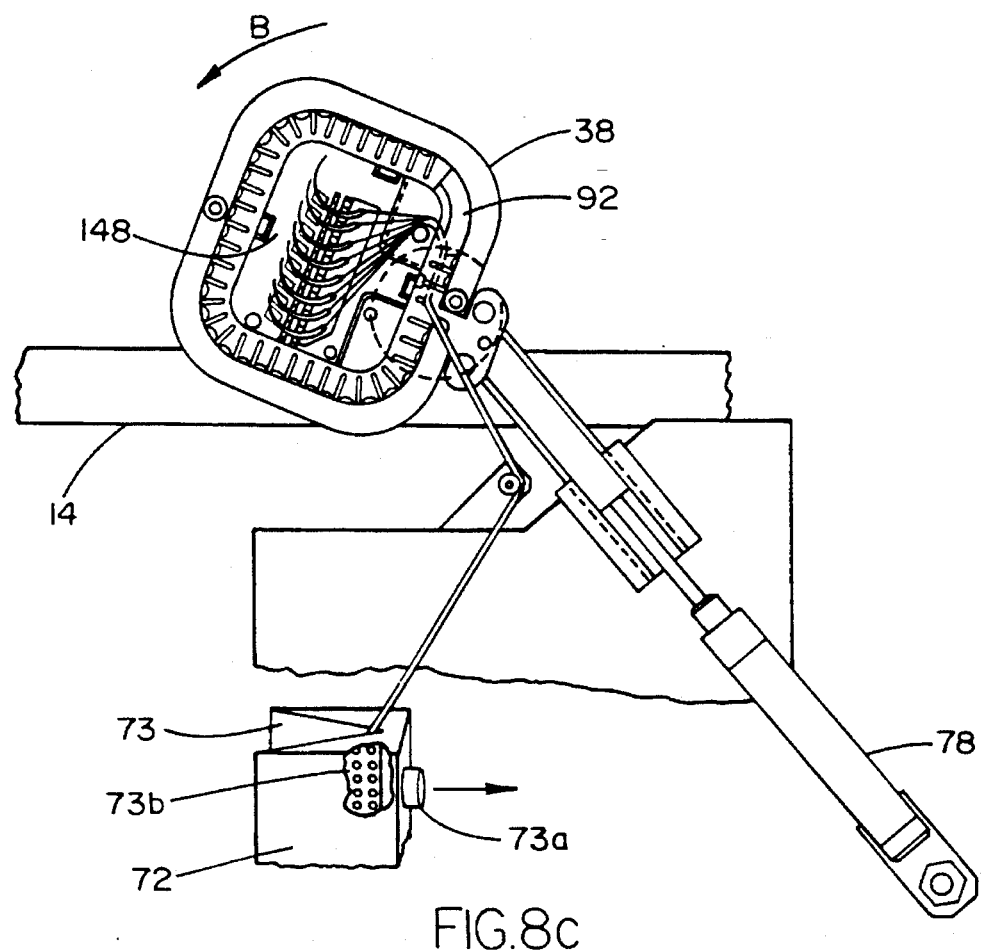

The functioning of the components of the stylus arrangement 76 for winding the suture into the tray is described in more extensive detail in connection with FIGS. 8a through 8c of the drawings, illustrating more specifically the vacuum unit 72, a pivotable lever which is operable in conjunction therewith for tightening and tensioning the suture bundle, and the stylus arrangement 76 cooperating with the resilient fingers 90 of the tray in order to feed the sutures into the channel in a winding motion as the tray is being rotated by its supporting platform 42 due to rotation of shaft 28 about axis 28a.

Figure 11:
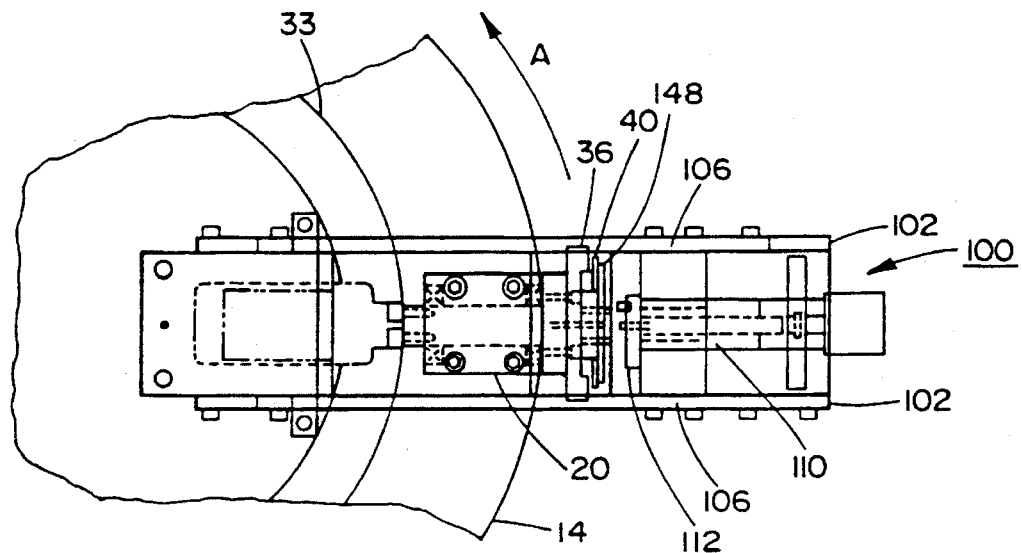
FIG. 11 illustrates a top view of the suture retaining unit of FIG. 10.
Figure 10:
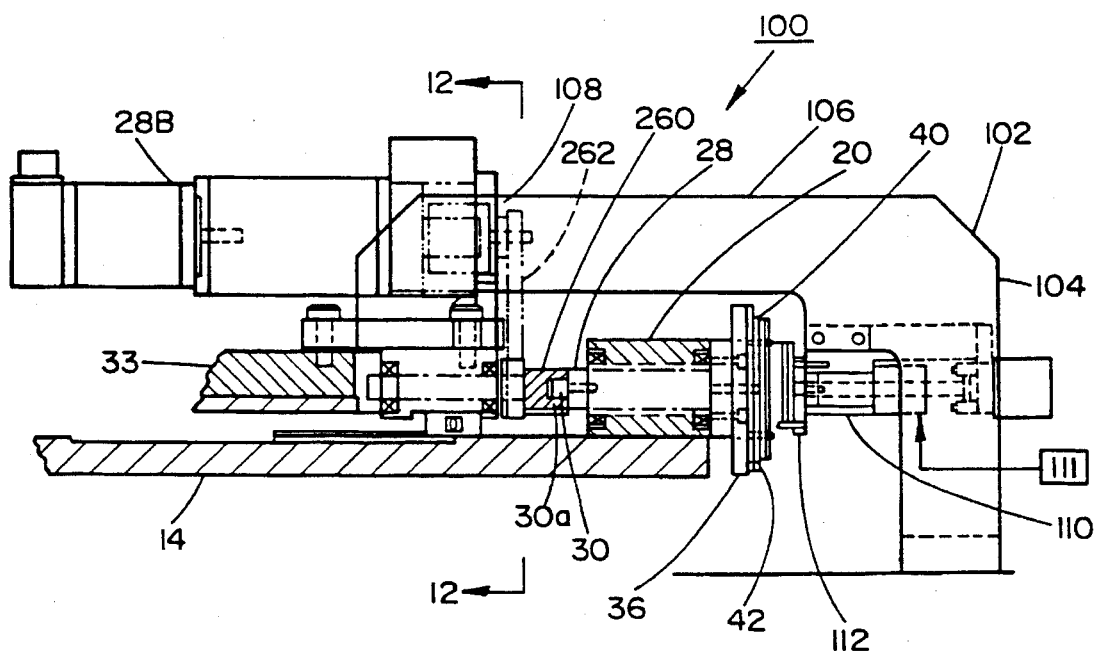
FIG. 10 illustrates a side view of a suture retaining unit in operative cooperation with the winding arrangement of FIGS. 8a through 8c.

Referring to FIGS. 10 and 11 of the drawings, adjacent the winding station, and extending over the stylus arrangement 76, there is arranged a tray restraint device 100 which comprises an L-shaped bracket 102 having one upright leg 104 thereof fastened to a stationary surface, and another portion 106 extending horizontally over the rotary turret 10 and the dial cam plate 33 thereon, and being operatively connected through a suitable drive arrangement 108 with an inner end of the shaft 28 extending through the housing 20 and which is connected with the cam plate 36 and plate 40 mounting the suture tray. A shaft 110 extends through the horizontal leg 106 of the stationary bracket 102 and upon initiation of the suture winding operation, is displaced axially towards the tray, either pneumatically or hydraulically by control means 111 such that a restraint plate 112 contacting the outwardly facing tray surface comes into operative engagement with at least a center portion thereof so as to inhibit the tray from being expelled outwardly from its mounted position on the platform 42 during the suture winding sequence. The interengagement of the restraint plate 112 and the tray, and the rotation imparted to the shaft 28, will cause the shaft 110 in the horizontal leg member 106 of the bracket 102 of the restraint arrangement to rotate in conjunction with the rotation of shaft 28. Upon completion of the winding procedures, the control means 111 shifts the restraint plate 112 to be shifted away from the tray into an inoperative position, so as to enable the tray on its tool nest 16 to be indexed to a further workstation by the advance of the rotary turret 10 in the direction of arrow A.

(6) At a further workstation, which may be an optional feature of the packaging machine, and to which the tray with the sutures having been wound into the channel 88 is adapted to be indexed, the tray and its contents are exposed to external visual inspection to facilitate a viewer to ascertain whether any of the sutures extend outwardly of the channel or tray, and whether the needles are properly parked in the tray and attached to their associated sutures.

(7) At a cover-applying and attaching workstation to which the tray is to be indexed from the preceding workstation, there is located a cover-applying apparatus 120 incorporating a pressing die structure 122 for attaching a cover to the tray, as illustrated in FIGS. 12 through 15 of the drawings, and for producing the suture package as shown in FIG. 22.

The apparatus 120 which is essentially stationarily mounted on a suitable fixed support proximate the perimeter of the rotary turret, includes an upstanding framework 124 which includes a pivot arm structure 126 hingedly mounted therein and being articulatable about a horizontal pivot axis 128 for movement between a vertical position facing the bottom end 130 of a cover supply hopper or chute 132 and a horizontal position facing a tray 148 mounted on platform 42 which has been indexed to this workstation. For purposes of illustration only, in FIG. 15 both the horizontal and vertical positions of the pivot arm 122 are illustrated, as pivotable along the direction of double-headed arrow C. A cover pressing die 123 is mounted at the outer or free end of the pivot arm 122.

Figure 13:
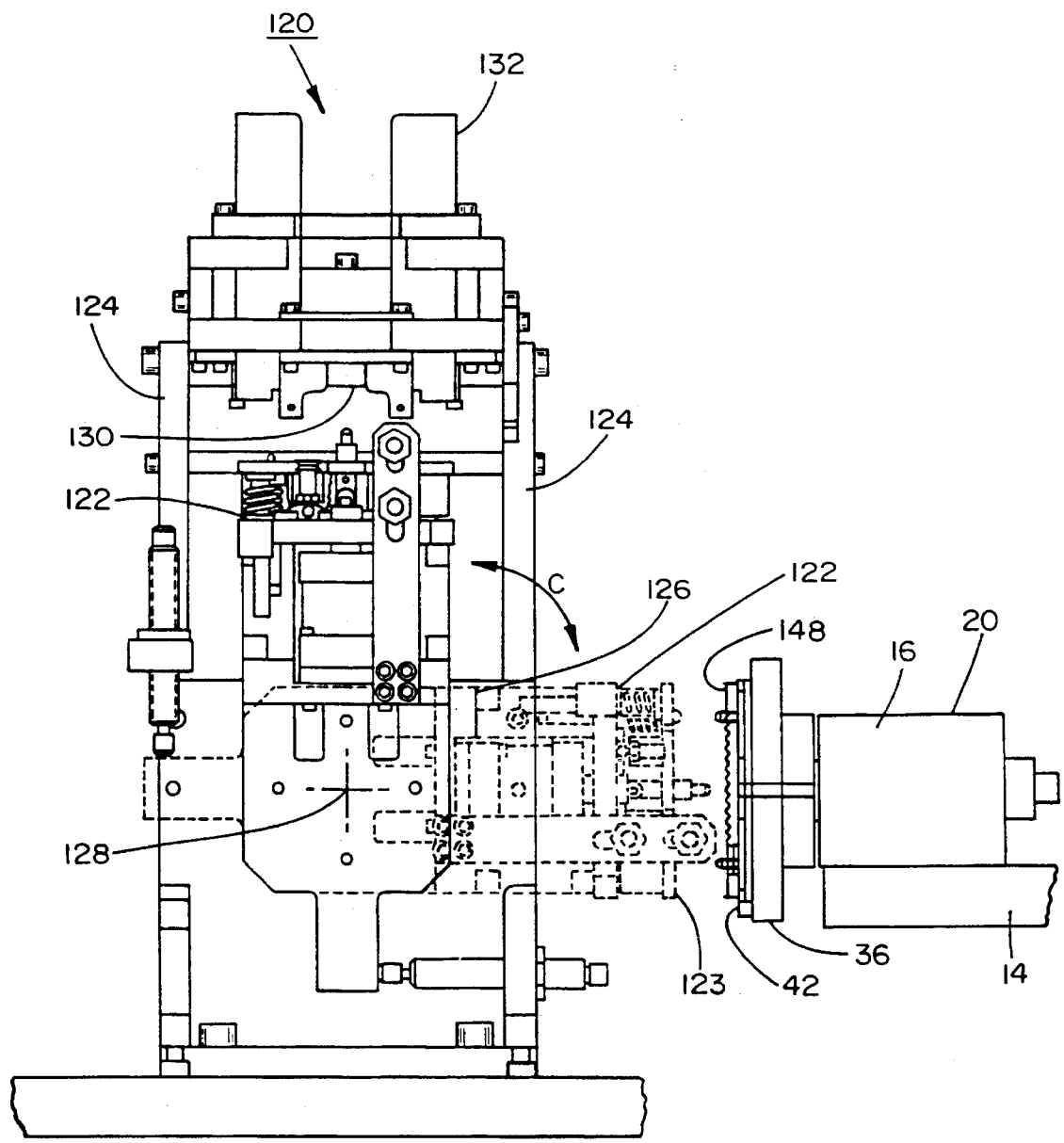
FIG. 13 illustrates a front elevational view of a cover-applying device in two operative conditions thereof.
Figure 15:
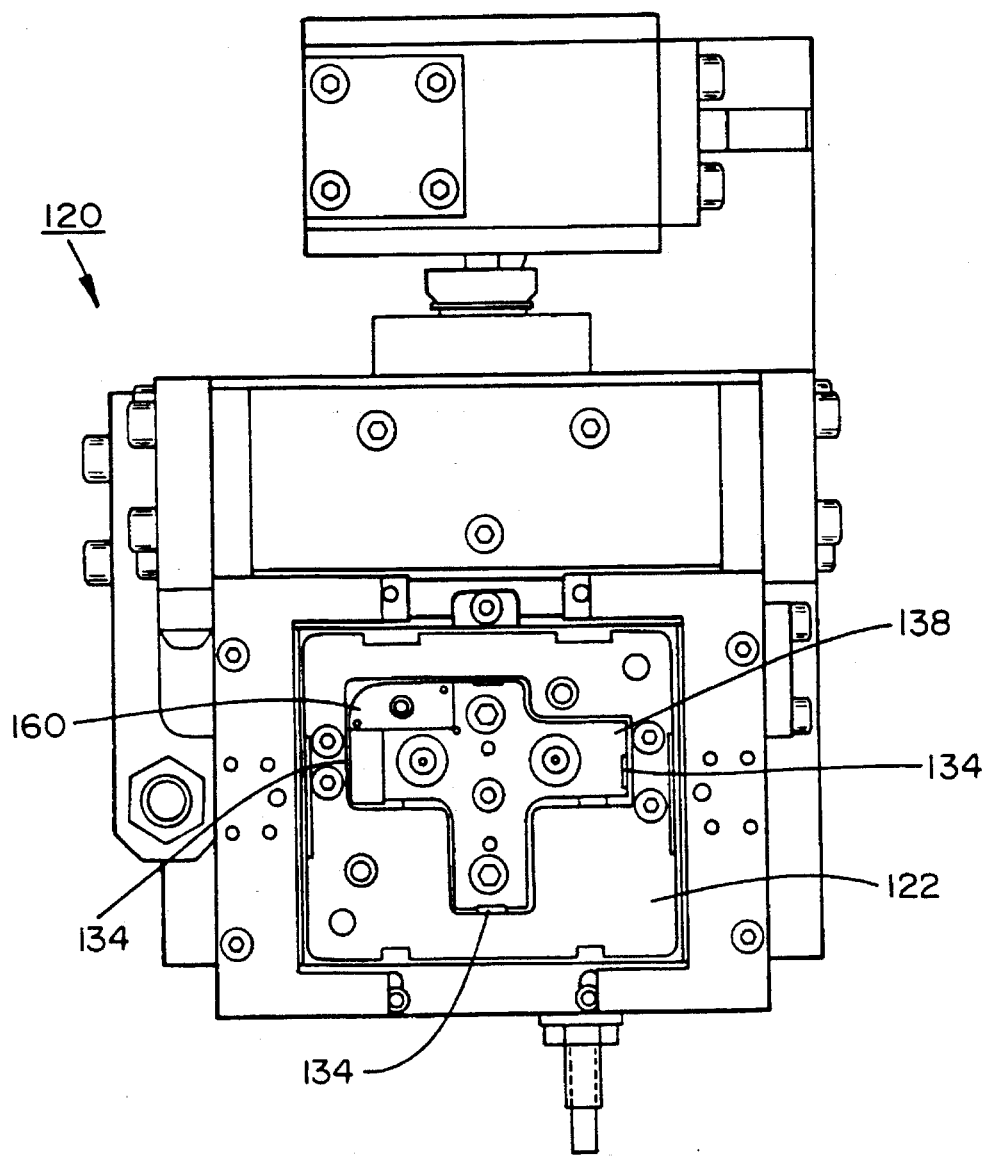
FIG. 15 illustrates a top plan view showing the cover-applying device and the cover-pressing die of FIG. 13.

The pivot arm structure 126 with the pressing die 123 therein, when in the upright position of FIG. 15, is adapted to engage and withdraw a tray cover which is dimensioned in conformance with the configuration of the tray, and in the presence of a tray having the needles and wound sutures contained therein at the workstation, the pivot arm 122 with the pressing die 123 at its outer free end and the cover positioned thereon is swung into horizontal axial alignment with the tray on the support platform 42, as shown in FIG. 13, and through suitable actuating means, such as by means of a pneumatic device 127, the arm 122 with pressing die 123 thereon is extended towards and into contact with the tray on platform 42 so as to position the cover on the tray. The pressing die 123 contains suitable surface structure, as shown in FIG. 15, for fastening the cover to the tray, as set forth hereinbelow.

The tray cover 150 is basically a flat cover which may be of a suitably imprinted paperboard or the like material, and is applied to be fastened to the tray 148 by means of pressing die 123, to form the suture package shown in FIG. 22. Herein, the outer dimensions of the cover, as previously mentioned, are substantially coextensive with the peripheral dimensions of the tray, and with the cover also having apertures 152 in registration with the upstanding guide pins 44 on the platform 42.

Figure 23:
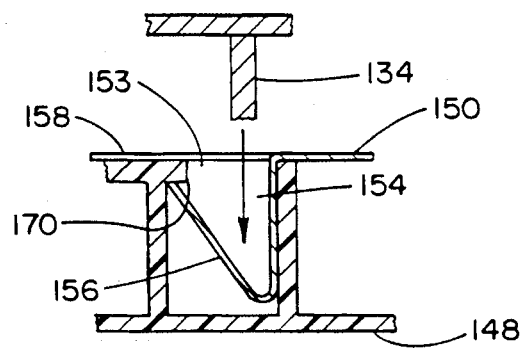
FIG. 23 illustrates, on an enlarged scale, a sectional view of one of the latching elements between the tray and an associated tray cover.

Hereby, the surface of the pressing die 123 facing the cover includes a surface portion 138 substantially in conformance with the flat surface of the cover 150 which has been superimposed on the tray 148, and includes three knife-like dies 134, preferably at three sides about the surface 138, and as shown in enlarged scale in FIG. 23 of the drawings, which will engage in slots 153 communicating with recessed portions 154 of the tray, and cause the cover 150 to be severed along three edges thereof, and thereby forming latching tabs 156 which are pressed in V-shapes downwardly into the respective recesses 154 so as to have the severed edge of the formed tab 156 at that particular location engage beneath a horizontal wall structure 158 of the tray 148 extending partially over the recess 154, thereby latching the cover 150 into cooperative engagement with the upper surface of the tray at three locations.

Concurrently, a further raised die surface portion 160 on the surface 138 of the pressing die 123 engages into a surface region 162 defined by suitable raised wall structure 164 on the tray 148. Die portion 160 and wall 166 form therealong a peripheral mutually cooperating cutting edge commensurate with the perimeter of surface area 162 so as to sever a portion 168 of the cover 150 in conformance with the area 162, and die portion 160 pushes the severed cover portion 168 downwardly into that area 162 of the tray so as to be secured therein severed from the remaining structure of cover 150. The severed portion 168 is permanently retained recessed within tray 148 by one or more ribs 170, as illustrated in FIGS. 21 and 22 which are formed in wall 166, so as to form a product-identifying label remaining in the tray upon subsequent detachment of the cover 150 from the tray 148.

(8) Responsive to indexed forward rotation of the rotary turret 10 to a successive workstation, the suture package consisting of the needle and suture-containing tray 148 and attached cover 150, as shown in FIG. 22, is positioned in alignment on the platform 42 with a package removal unit 170, as illustrated in FIGS. 16 to 18. In FIG. 16 of the drawings, a pivoting arm structure 173 is illustrated in both its horizontal and vertical operative positions, being pivotable along the direction of double-headed arrow D. Suitable grippers 172 which are pivotably mounted on the pivoting arm structure 173 which is journaled on a stationary frame 174 the latter of which is somewhat similar in structure to the framework 124 of the cover-applying apparatus 120, are pivotable into a horizontal orientation for engagement with the suture package so as to be able to grip and withdraw the suture package from its support surface or platform 42. The grippers 172 with the therewith clamped suture package are then adapted to be pivoted upwardly into a vertical orientation by means of pivoting arm structure 173 into alignment with an opening 176 in the bottom 178 of a hopper or chute 180. The opening is provided for receiving a stack of completed suture packages through the upward pushing action of a ram 182 biasing the suture packages into the chute 180, as shown in FIG. 16 and in the enlarged detail of FIG. 18. The bottom 178 of the chute includes a retaining lip 184 to prevent the suture packages from falling downwardly out of the chute. Alternatively, this particular, basically optional structure for removing the completed suture package from the support surface may be eliminated, if desired, and replaced by a manual suture package-removing operation.

From the chute 180, the suture packages which are stacked therein may then be removed either through the intermediary of a further mechanism (not shown) or manually transported for additional processing; for example, such as sterilizing, and/or additional overwrapping, or the like.

OPERATION OF THE AUTOMATED PACKAGING MACHINE

The operation of each workstation, in summation, is essentially as follows; discussed hereinbelow with regard to a single operating cycle in the formation of a single suture package:

Operation of Tray Loading Workstation (1)

At this workstation, the support surface or platform 42 on the plate 40 for receiving an empty injection-molded plastic tray 148, as illustrated in FIGS. 3 to 5, is indexed by rotary turret 10 into alignment with a tray dispensing arrangement (not shown) from which a tray is gripped and removed from a stack of trays and pivoted into alignment with platform 42 and advanced thereon so as to cause the apertures in the tray to be positioned in registration on the guide pins 44 projecting from the platform 42. Thereupon, the tray dispensing arrangement may be withdrawn, and placed into position to receive a successive tray which, when the first-mentioned tray is indexed forwardly by the rotary turret 10 to the next workstation, will enable a further tray to be mounted on a successive platform on a tool nest 16 located on the rotary turret 10. At that time, the vertically extending plate 40 with platform 42 and the cam plate 36 on which it is arranged are oriented in a manner with the side edges thereof vertically extending, as shown in FIGS. 3 through 6 of the drawings. Alternatively, if desired, this procedure of positioning a tray on the platform 42 may be manually implemented, thereby eliminating the foregoing operative structure.

Upon withdrawal of gripping members having positioned the empty tray 148 on the support platform 42, the rotary turret 10 is now in a condition to be indexed or rotationally advanced forwardly to the next workstation, in the direction of arrow A.

Operation of Tray Detection Workstation (2)

This particular workstation, which is essentially optional, has the sensor 50, as shown in FIGS. 19 and 20, positioned in front of the rotary turret 10, such that upon the platform 42 on the rotary turret mounting a tray being positioned in indexed alignment with the sensor 50, this enables the latter to ascertain the presence of a tray 148 and its appropriate support on the guide pins 44 of the support platform 42. Upon a determination having been transmitted by the sensor to that effect to the operating and drive components (not shown) of the machine, the indexing rotary turret 10 is now in a condition to advance the tray on its support platform 42 to the next workstation.

Operation of Needle and Suture Inserting Workstation (3)

At this workstation, suitable needle grippers on needle-feeding mechanism 56 successively position and park needles in the needle clamping structure formed in the center portion of the tray 148, as illustrated in FIG. 21 of the drawings.

Figure 24:
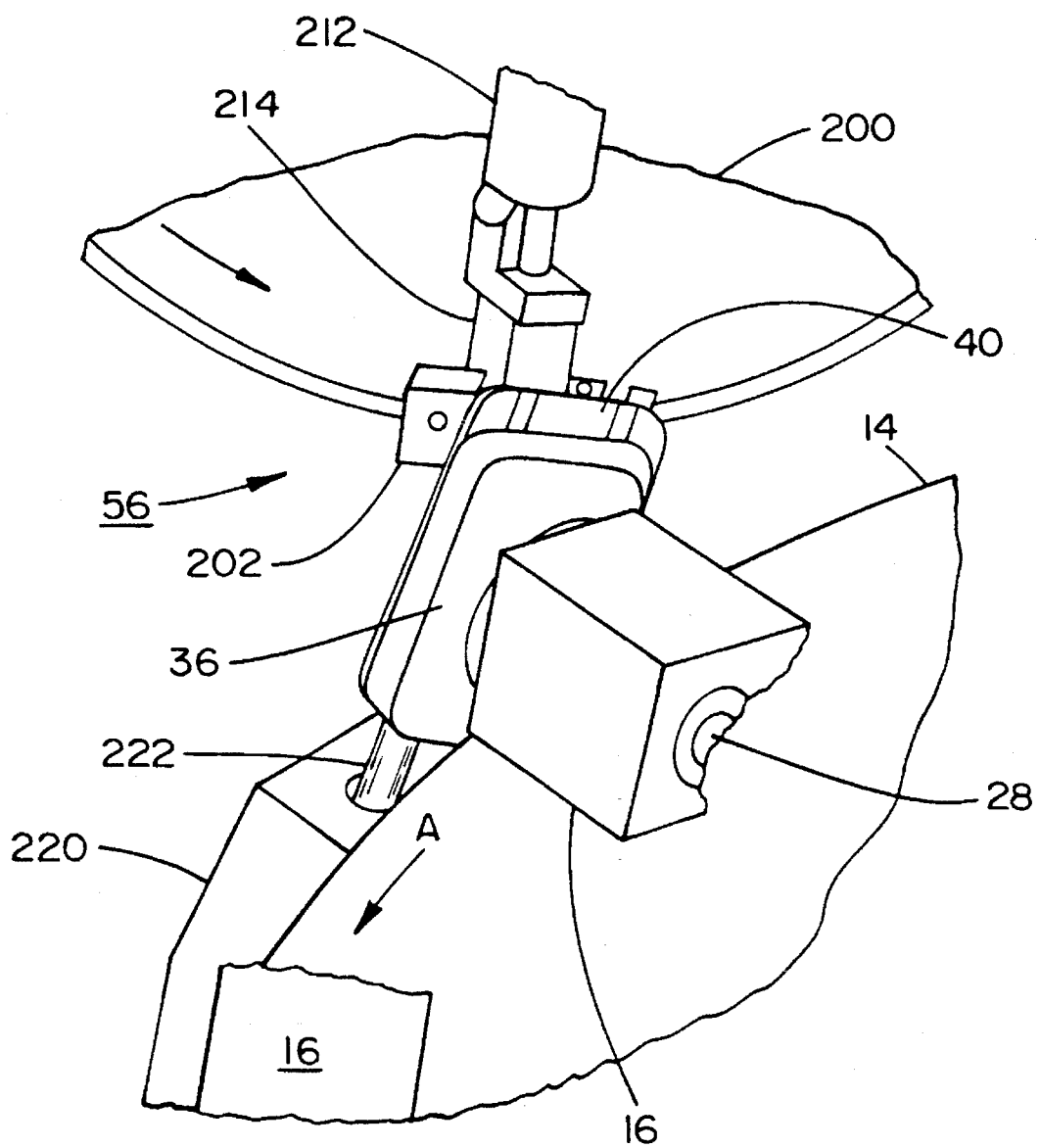
FIG. 24 illustrates, generally diagrammatically, a perspective view of a mechanism for transferring needles with attached sutures into a suture tray mounted on a tool nest of the main rotary turret.

As is illustrated FIG. 24, an empty tray 148 has been previously mounted on a tool nest 16 of the main rotary turret 10. The tool nest 16 includes the plate 40 having the tray-supporting platform 42 which may be registered in increments so that the empty tray 148 may receive eight (8) armed needles. While the preferred embodiment described herein describes the invention with respect to a reduced size organizer package (RSO) which is adapted to be supplied with eight (8) needles, it should be understood that the invention could be used with equal efficiency with a single-needle package or other amounts of needles.

Figure 25A:
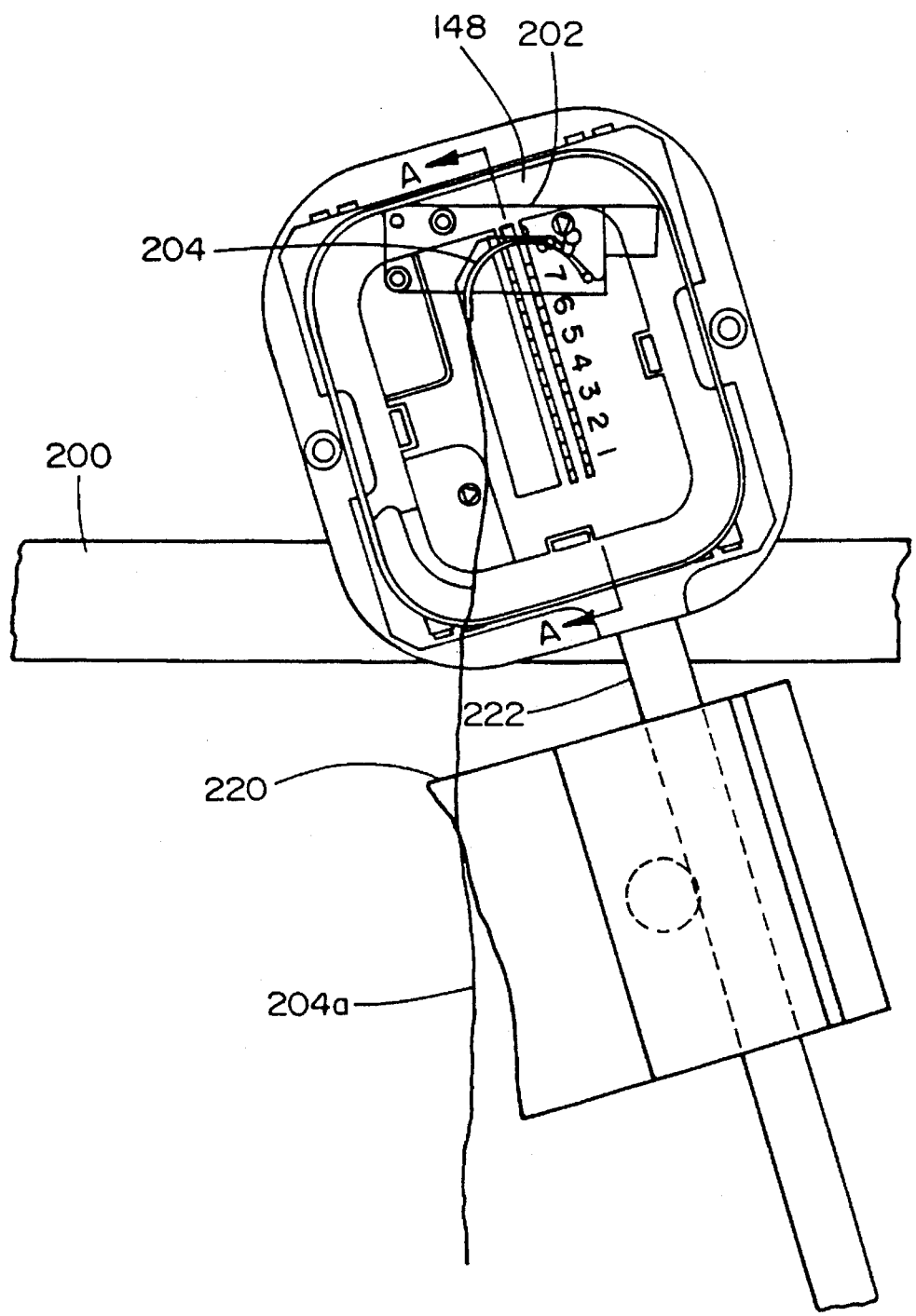
FIG. 25a illustrates, on an enlarged scale, the suture tray of FIG. 24 with the device for elevating the tray to enable a plurality of needles to be parked therein.
Figures 25B, 25C:
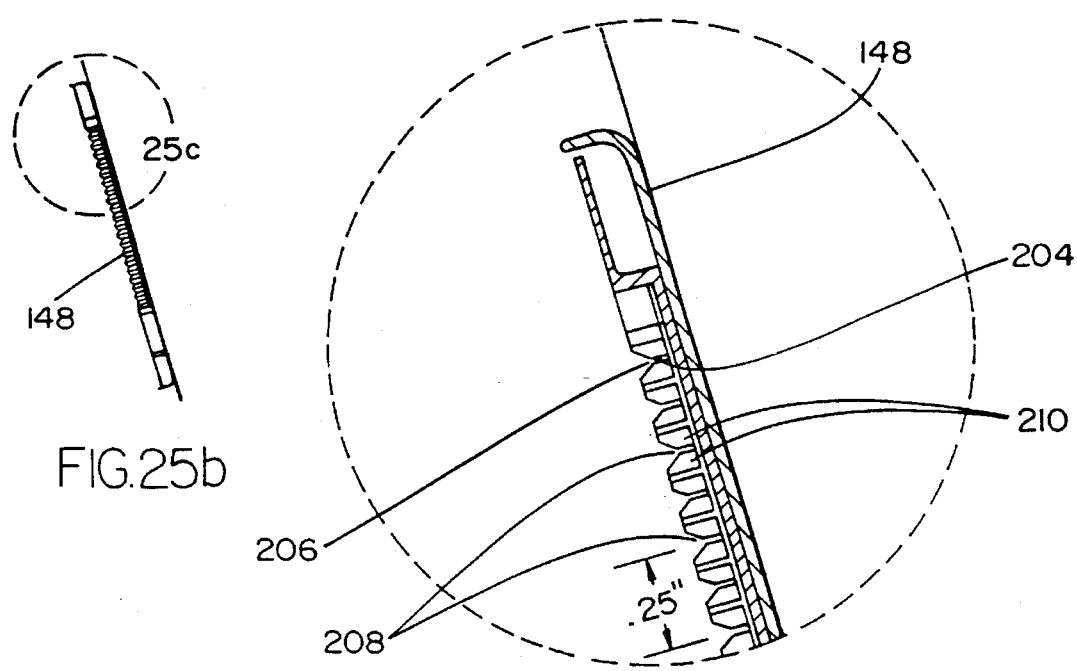
FIG. 25b illustrates a side view of the suture tray.
FIG. 25c illustrates an enlarged fragmentary view of the encircled portion of FIG. 25b.

The face of the empty tray 148 illustrated in FIGS. 25a through 25c shows a plurality of grooves between raised tray portions forming clamping structures for accommodating the sequential placement of eight armed surgical needles. In order to load the first armed needle into the empty tray 148, the tool nest 16 is indexed to workstation (3) as shown in FIG. 24. Simultaneous therewith, a rotary swage dial 200 as disclosed in the copending application (Attorney Docket 8922), indexes a multi-axis gripper 202 to workstation (3). Then, the multi-axis gripper 202 is extended towards the empty tray 148 to deposit an armed needle 204 within a first pair 206 of the eight paired sets of needle receiving notches 208 that are formed between protruding portions 210 in the bottom surface of the tray. In the preferred embodiment, each paired set of notches 206 is consecutively numbered and spaced approximately 0.25 inches apart, as shown in FIG. 25c. In the disclosed embodiment, the first needle 204 loaded is in the eighth position as shown in FIG. 25a. As illustrated in FIGS. 24 and 25a through 26c, the tool nest 16 assembly and, consequently, the empty tray 148 is slightly tilted counter-clockwise from the vertical with respect to the orientation of the multi-axis gripper 202 so that the curved needle will be accurately deposited within the notches formed in the package. This tilt, which may be about 10°–20°, and preferably 16° from the vertical, may be effected due to the contact between the cams 30 and an angled or sloped camming surface on cam dial plate 33 at workstation (3). As a result of this tilting offset, the needles are slightly shifted relative to each other, and the sutures depending downwardly therefrom will not tend to tangle with each other. Under control of the control system computer, a solenoid 212 then actuates a push rod 214 to depress the plunger on the multi-axis gripper 202 so that it may release its grip of the armed needle 204 in the manner described above.

As shown in FIGS. 24, 25a through 25, and 26a and 26b, there is located at the workstation (3) a package elevator assembly 220 that registers the empty tray 148 to receive eight individual armed needles, one at a time.

As illustrated in drawings, the tool nest 16 includes the fixed body structure 20 containing the rotatable shaft 28 at which there is mounted the package tray holding platform or support surface 42 and the previously-described structure. Most of the turret stations, which as shown in FIG. 1 of the drawings are in this case eight (8) in number, require that the tool nest 16 is precisely maintained in a non-rotated vertical position, as illustrated specifically in FIGS. 3 and 5. This particular vertical orientation is maintained in that the circular stationary cam dial plate 33 extending between the collective workstations is contacted by the two cam followers 30, which are in the form of cam rollers 30a and 30b mounted on shaft 28 so as to straddle the longitudinal centerline of the latter, for each of the tool nests mounted on turret 10.

Figure 26A:
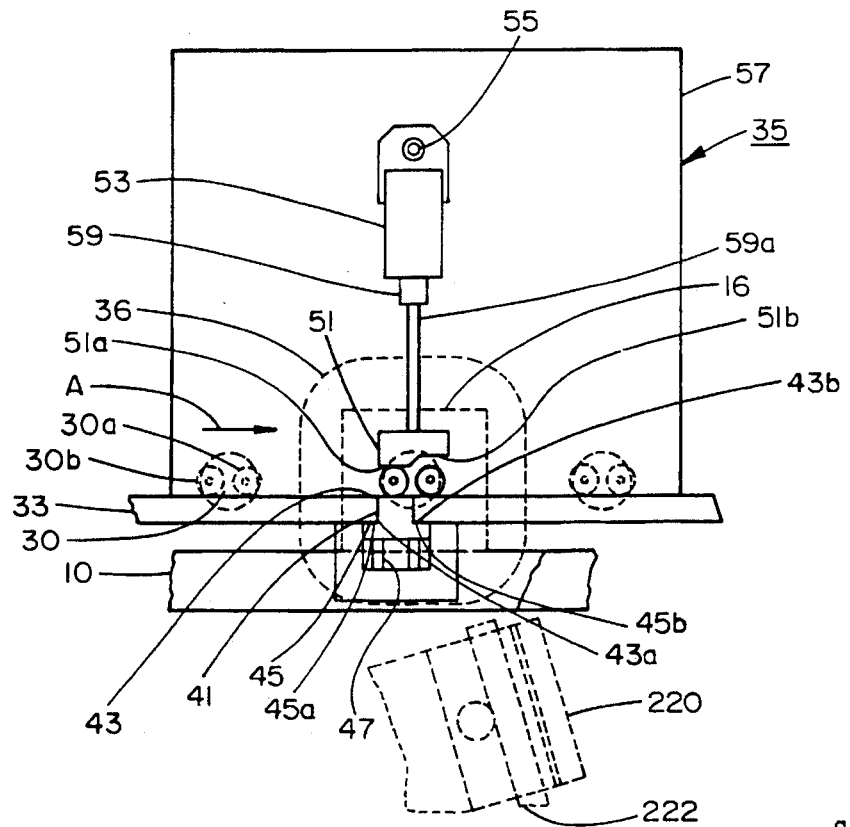
FIGS. 26a through 26c illustrate tilting mechanisms which are operatively associated with the tray elevating device of FIG. 25.

Prior to needle insertion at the needle inserting workstation, the tray 148 is adapted to be rotated into a tilted orientation through preferably an angle of 16° counter-clockwise so that needles are to be positioned in a correct array and orientation in the needle park structure of the tray. This is attained by a tool nest rotating structure, as illustrated in drawing FIGS. 26a and 26b, operating in functional sequence essentially as follows:

FIG. 26a is an elevational view of the needle inserting station showing the indexing turret 10 upon which the tool nest 16 has been mounted, consisting of the tray holding plate 40, including the tray supporting surface or platform 42. The shaft 28 is mounted in suitable bearings, (i.e. 29a and 29b) so as to be freely rotatable within the housing 20 of the tool nest 16, if required to do so.

As a specific tool nest 16 which has the tray mounted thereon at the first workstation, and which is adapted to be supplied with the needles, enters the needle and suture inserting workstation, in the direction of arrow A, the tool nest 16 enters the tilt mechanism 35. The two cam followers 30, hereinafter designated as cam rollers 30a and 30b, roll along the upper surface of the stationary cam dial plate 33, as illustrated by phantom lines at the left-hand side, and then pass into the tilt mechanism 35 stopping in the position shown in solid lines at the center in FIG. 26b.

A track section 41 which consists of an insert having upper surface 43 normally in coplanar relationship with the upper surface of the cam dial plate 33, and which extends through a cutout 45 formed in the cam dial plate 33, has its uppermost position determined by shoulders 43a and 43b bearingly contacting against mating lower surfaces 45a and 45b on the lower side of the stationary cam dial plate 33. Normally, the track section 41 is biased upwardly into the cutout 45 under the urging of compression springs 47 which are supported against a suitable spring support member 49. At this position, the upper surface 43 of the insert 41 is in the same plane as the upper surface of the cam dial plate 33.

A displacement cam element 51 is in a normally raised position above the cam rollers 30a, 30b to enable the latter to roll into the index mechanism 39 workstation and enabling the tilting mechanism to operate without any interference of components in the rest or dwelling position, as illustrated.

In order to rotate or tilt the tool nest 16 for appropriate needle insertion, an air cylinder 53 of the mechanism 51, which is attached by means of suitable screws 55 to a plate structure 57 mounted above the camming dial plate 33; through a cylinder rod 59a of a piston device 59 causes the downward displacement of the cam element 51. This downward motion is guided by a suitable sliding device (not shown). The lower cam surface 51a of the displacement cam element 51 exerts a downward force against cam roller 30b which, in turn, forces the insert 41 to move downwardly within the cutout 45 provided in the cam dial plate 33, compressing the springs 47, and thereby rotating the shaft 28 in the housing 20 of the tool nest 16 counter-clockwise about axis 28a. The downward movement continues until the upper surface portion 51b of the displacement cam element 51 contacts the other cam roller 30a which has been displaced upwardly an amount equal to the downward displacement of cam roller 30b, and the system reaches the end of travel, causing the air cylinder to maintain the position, as shown in FIG. 26a. The foregoing results in a rotational movement of shaft 28 to which the cam rollers 30a and 30b are fastened, and resultingly of the support surface 42 and tray mounted at the opposite other end of the shaft 28 in a counter-clockwise direction, preferably to a tilting angle of 16°.

After completion of the needle insertion operation, this sequence is reversed in that the air cylinder receives compressed air so as to raise the displacement cam element 51. As a consequence, the springs 47 cause the insert 41 to be biased upwardly, causing the upper surface 43 thereof to press against the cam roller 30b and causing shaft 28 to rotate clockwise. This continues until the shoulders 43a, 43b contact the stationary surfaces 45a, 45b at the lower side of the cam dial plate 33, thereby stopping this rotational motion. This clockwise rotation of the shaft 28 causes the cam roller 30a to move a lower position until it contacts the upper surface 43 of the insert 41 which is now located in the same plane as the upper surface of the stationary cam dial plate 33. A suitable switch, for example, a proximity switch (not shown) now indicates that all of the mechanical components of this arrangement have been returned to the original position of FIG. 26a, and the turret 10 indexes the tool nest forward for the next operating cycle. FIG. 26b shows a dashed line representation of the cam rollers 30a and 30b rolling on the surface of the tool cam dial plate 33 towards the right, and the shaft 28 being displaced from this workstation.

This aspect provides a structure of providing a rotary tilted positioning of a product on an indexing turret, in this application rotation of the shaft 28 and tilting the package or tray mounted thereon by means of the support plate 36 and platform 42, such as through an angle within the range of 10° to 30°, and preferably about 16°, due to the parallel offset distance between the camming surfaces 51a, 51b on the displacement cam element 51 which contact the cam rollers 30a and 30b.

Figure 26C:
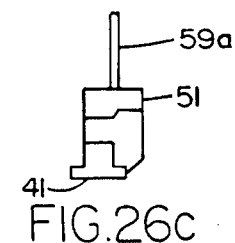
Figure 26B:
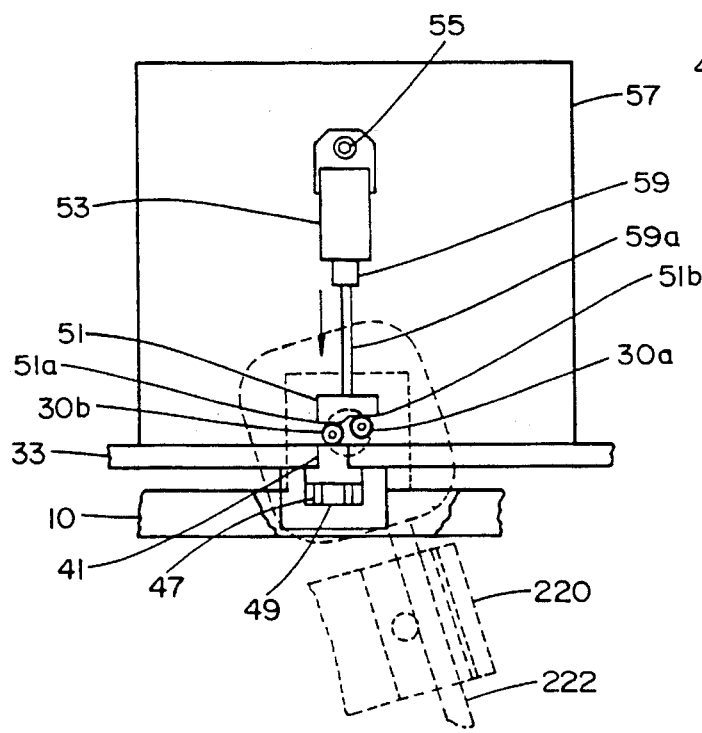

In FIG. 26c there is disclosed schematically an alternative design, similar to the foregoing, however, in which the individual structural components of the tilting arrangement are combined into an integral modular unit.

A shaft 222 of elevator assembly 220, as shown in FIG. 25a, raises the plate 40 essentially vertically but slightly skewed (at about 16°) in 0.25 inch increments to sequentially receive eight needles from the multi-axis gripper 202 as described above. In this embodiment, the rotation of the swage dial 200 supplying armed needles from a pull-test station (not shown) at a rate of approximately 60/min. is synchronized with the vertical incrementing of the plate 40 mounting the tray 148 to maximize production rates. For example, after inserting the first armed needle 204 into the empty tray 148 into the paired notches numbered "8" as described above, the elevator shaft 222 raises the plate 40 vertically for 0.25 inches so that the next armed needle 204 may be deposited in the pair of notches 206 numbered "7." Simultaneous with the registering of the tool nest plate 40, the rotary swage dial 200 indexes the next multi-axis gripper 202 carrying the second armed needle, so that it may insert the next needle in the second position (notch "7") of the tray 148. This process takes place eight (8) times to fill a reduced size organizer package containing eight (8) armed surgical needles. After the eighth needle has been inserted in the package, the elevator assembly 220 retracts the elevator shaft 222 by conventional means such as a pneumatic air cylinder (not shown). Thus, the tray 148 which is now equipped with eight armed needles is in its initial position on the tool nest 16 and the tray is ready for further treatment at successive workstations.

Upon the requisite number of needles having been parked in the tray; for example, eight needles, the grippers 202 for transporting needles to the tray cease operation, and the rotary turret 10 indexes to the next workstation, while a subsequent tray may be positioned indexed in front of the needle dispensing unit so as to, in turn, be capable of being equipped with needles and attached sutures, as was the preceding tray 148.

Operation of Needle Detecting Assembly (4)

This workstation, which is essentially an optional workstation on the machine following the needle inserting workstation (3) along the rotational indexed movement of rotary turret 10 in the direction of arrow A, has the needle detector arrangement 60 comprising a plurality of sensors 62 forwardly extended into close proximity to the surface of the tray containing the needles and depending sutures. This will provide information to a program control system that there has been ascertained that the appropriate numbers of needles have been inserted into and "parked" in the tray at workstation (3). Upon such a determination having been made by the sensors 62 and the information transmitted to the machine program control system, the rotary turret or turntable 10 is then indexed forward to the next workstation.

Operation of Suture Winding Workstation (5)

As the tray 148 with the parked array of needles therein and depending sutures reaches this workstation in that the rotary turret 10 has been indexed forward, the downwardly depending sutures hanging loosely from the tray 148 and from the needles to which they are attached, are essentially collected in the vacuum device 72 which has an internal V-section 73 wherein a generated vacuum applies tension to the sutures and collects and stretches them into a bundled strand. Concurrently, as shown in FIGS. 8a through 8c, the entire tray supporting platform 42 and cam plate member 36 are subjected to rotation about axis 28a in the direction of arrow B responsive to the operation of shaft 28 by means of a programmable servomotor 28b, as illustrated schematically in FIGS. 10 and 11.

At first, as shown in FIG. 8a, wherein the rotary turret 10 has just indexed to the right to this workstation by bringing a subsequent tray 148 mounted on its platform 42 into the winding index position, the bundle of sutures, in this instance, eight sutures each respectively attached to one of the surgical needles parked in the tray, and which sutures hang downwardly from the tray enter the vacuum gathering device 72 which has the vertical V-shape 73. The vacuum is created by a vacuum being pulled from an exhaust port 73a which creates an airflow into the "V" shape through suitable vent holes 73b.

As shown in FIG. 8a, the turret index which has moved the tray to the right is complete, and this motion has dwelled in preparation for the winding function for the sutures.

The suture winding workstation as illustrated in FIG. 1 of the turret 10 includes structure for rotating the package and to accomplish the suture winding operation. This is accomplished by a motorized driving mechanism as shown in FIGS. 12a through 12c and 10. The primary main turret 14 as shown in FIG. 10 which has the tool nest 16 thereon containing shaft 28 mounted in suitable bearings 29a, 29b in housing 20.

Figure 12A:
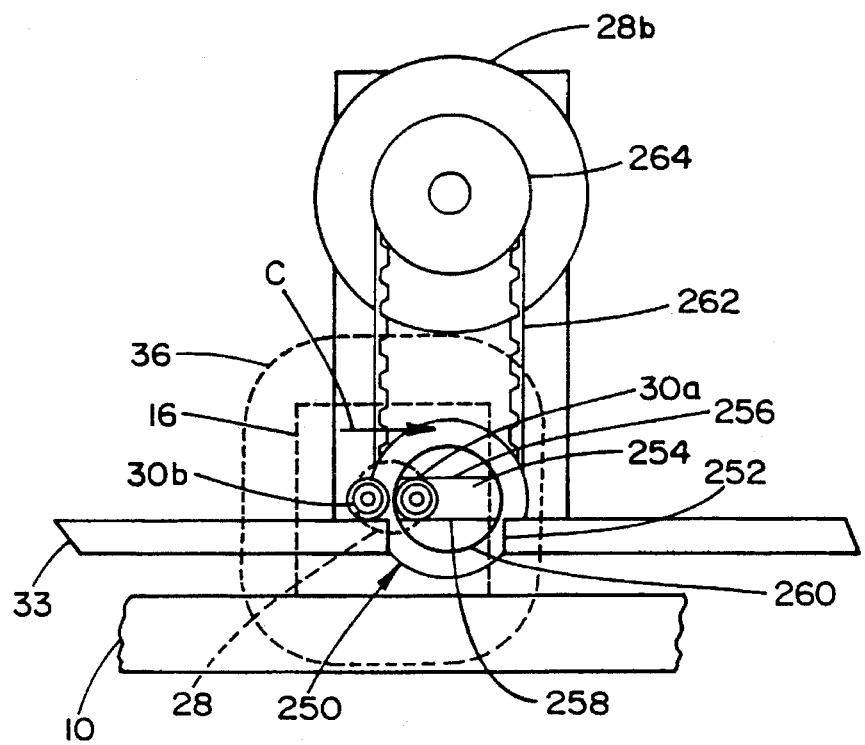
FIGS. 12a through 12c illustrate, respectively, operative drive structure for the suture winding arrangement, shown on an enlarged scale, taken along line 12—12 in FIG. 10.
Figure 12B:
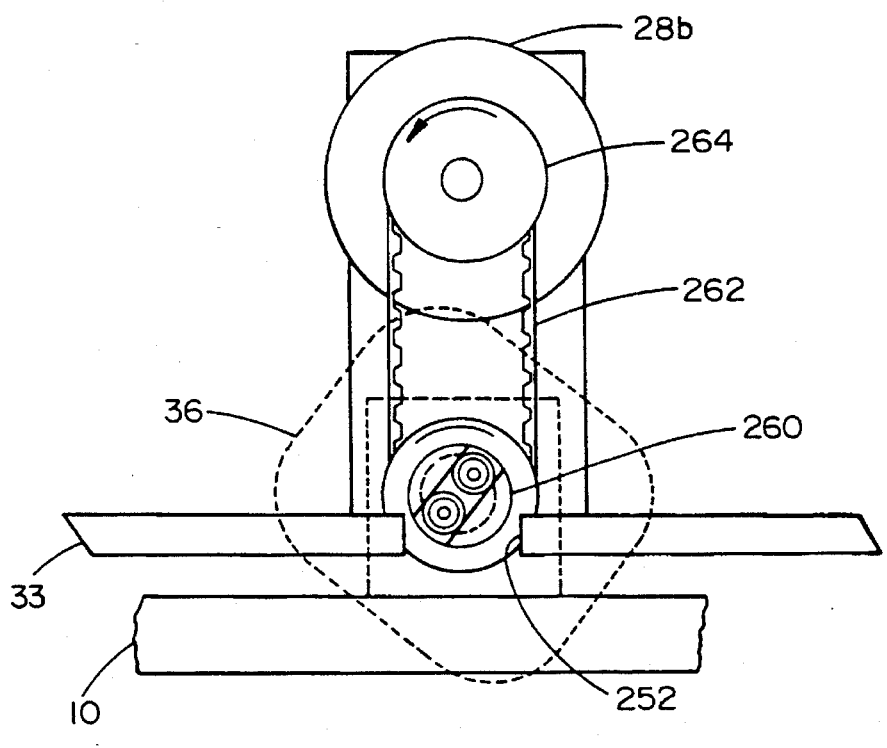
Figure 12C:
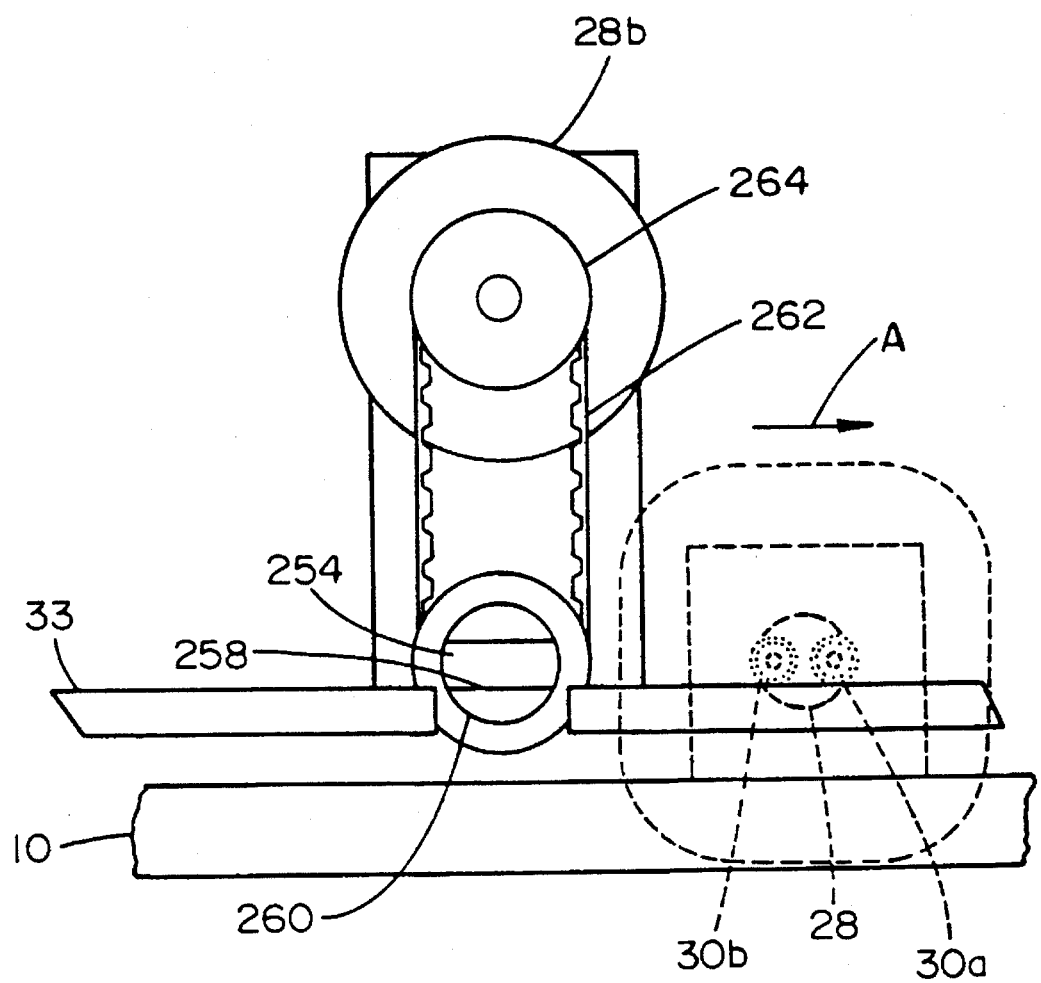

As the winding machine is indexed for a next suture winding cycle, the tool nest 16 is moved into the rotational station 250 as shown in FIG. 12a, indicated by arrow C. The cam rollers 30a and 30b cross a gap 252 provided in the stationary cam dial plate 33 and enter a slot 254 formed by opposite parallel surfaces 256, 258 formed in a driven roller 260, the latter of which extends partly into the gap 252 produced by a cutout provided in the cam dial plate 33. The lower surface 258 of slot 254 is normally substantially in coplanar and axial alignment with the upper surface of the cam dial plate 33 enabling the rollers 30a and 30b to be centered therein. This centering action takes place in a dwell position of the turret 10 in the suture winding workstation, whereby the longitudinal centerline 28a of shaft 28 is coincident with the centerline of the driven roller 260. The drive roller 260 is mounted in suitable bearings such as to be able to be rotated by the servomotor 28b driving a timing belt 262 extending from a driving roller 264 to the driven roller 260 so as to operatively interconnect the rollers 260, 264.

When the winding cycle is started at the suture winding station, as shown in FIG. 8a, the servomotor 28b drives the driving roller 264 which, in turn, drives the driven roller 260 through the timing belt 262. At the end of the winding operation, the driven roller 260 is stopped to cause a horizontal orientation to be assumed by the slot 254 and the opposite surfaces of the slot are coplanar or coextensive with the upper surface of the cam dial plate 33. The turret 10 then indexes in the direction of arrow D, advancing the cam rollers 30a and 30b out of the slot 254 of the driven roller 260 and onto the upper surface of the tool camming plate 33, thereby locking the support plate and tray into a vertical tray orientation which is secured against rotation. A suitable switch, such as a proximity switch (not shown) assures that the driven roller 260 is in the horizontal slot orientation before indexing the turret 10 forwardly, thereby preventing any mechanical interference between components which could damage the latter. The rollers 260 and 264 may be suitable sprocket wheels, and the timing belt 262 a sprocket belt or chain.

The programmable servomotor 28b which rotates shaft 28 having the tool nest 16 fastened thereto and, effectively, the support platform 42 and cam plate 36 for the tray 148 about its center rotational axis 28a has completed an initial counter-clockwise rotation in the direction of arrow B, causing the suture bundle to wrap around a pin 75 which protrudes from the suture tray towards the viewer, when looking into the plane of the drawing. This rotation pulls the suture bundle partially out of the vacuum gathering device 72, which imparts a predetermined tension to the suture bundle causing it to become straight and the individual strands or sutures to be collected into a parallel and tightly confined group. The winding stylus assembly 76 which is mounted on a stationary plate is shown in its retracted position in cylinder 78, as it is during turret index.

In FIG. 8b, the subsequent phase of the winding operation is illustrated wherein a suture positioning arm 77 has been actuated to rotate clockwise, bringing a roller 77a to bear against the suture bundle, thereby implementing two functions:

(a) The suture bundle length is increased between the pin 75 and the vacuum device 72 causing additional suture length to be drawn out of the vacuum device and resulting in a tighter more confined suture bundle.

(b) Moreover, the foregoing displaces the suture bundle towards the right, so that a winding stylus 79 having fingers or legs 79a and 79b can straddle the bundle in the now extended position of the stylus arrangement, and be dropped on the floor of the tray channel 88 (in a motion perpendicular to the plane of view into the drawing) with a reasonable assurance that the bundle strands will not become pinched or fall outside of the stylus legs 79a, 79b.

Hereby, FIG. 8b also discloses the winding stylus assembly 76 extended towards the tray 148 by the extension of the air cylinder 81 until the stylus guide rollers 74a, 74b contact the peripheral cam surface 38 of the tool nest. The air cylinder maintains a force against the rollers 74a, 74b during rotation of the tray 148 for winding, acting in a manner of a spring as the rollers force the stylus head 79 and the slide 83 to oscillate. The slide oscillates within the stationary slide holder 85.

Reverting to FIG. 8c, this discloses the commencement of the tray rotation on the support surface 42 for effectuating winding of the sutures. The air cylinder exerts a constant force on the slide 83, and through a pivot pin 87 to the roller assembly 74a, 74b. The stylus 79, which is mounted in the roller assembly is maintained at 90° relative to the suture tract by this action. The enlarged encircled detail view of FIG. 9c discloses the suture bundle after it is positioned below the resilient suture-retaining tray fingers 90. This also illustrates the manner in which the stylus 79 plows under the tray fingers, lowering them progressively as it leads the suture bundle therebeneath and guides the bundle into the peripheral channel 88 of the tray 148. As this winding takes place, the vacuum device 72 maintains a constant essentially gentle tension on the suture bundle as it is withdrawn therefrom, and this action continues until the suture bundle ends withdrawn from the vacuum device and are fully inserted by the stylus 79 under the resilient tray fingers 90 into the peripheral suture tray channel 88. At this final point of the winding cycle, the tool nest 16 mounting the tray is rotated to position the stylus in the suture channel window or gap 92, as shown in FIG. 21, whereupon the stylus 79 is raised upwardly out of the gap 92 in the channel 88 of the tray 148 and the air cylinder 81 retracts the stylus assembly, i.e. the piston rod mounting the latter, to the position shown in FIG. 9a. Hereby, rotation of the tool nest mounting the tray with the needles parked therein and the sutures wound into the channel 88 continues in a counter-clockwise direction until the needle part is vertical with the needle points extending downwardly, and the rotary turret 10 is in a position to be indexed for the next cycle, in effect, for receiving a subsequent tray.

During the foregoing suture winding sequence of operation, as previously mentioned, the restraint device 100 continually maintains its contact with the tray so as to prevent the tray and the contents therein from being expelled from the support platform 42 on which the tray 148 is mounted. The restraint device 100 is withdrawn from the tray 148 upon completion of the suture-winding procedure to enable the continued forward indexing rotation of rotary turret 10.

Operation of Visual Inspection Workstation (6)

As the rotary turret 10 is indexed forwardly subsequent to completion of the suture winding procedure, so as to enable a successive tray 148 to reach the suture winding workstation (5), the preceding tray 148 with the sutures having been wound therein is indexed forwardly in the direction of arrow A by the rotary turret 10 and optionally exposed to external visual inspection in order to be able to ascertain that all of the needles are parked, the sutures have been properly wound into the tray channel and that no suture portions hang outwardly of the tray channel 88.

Operation of Cover Applying and Attaching Station (7)

Figure 14:
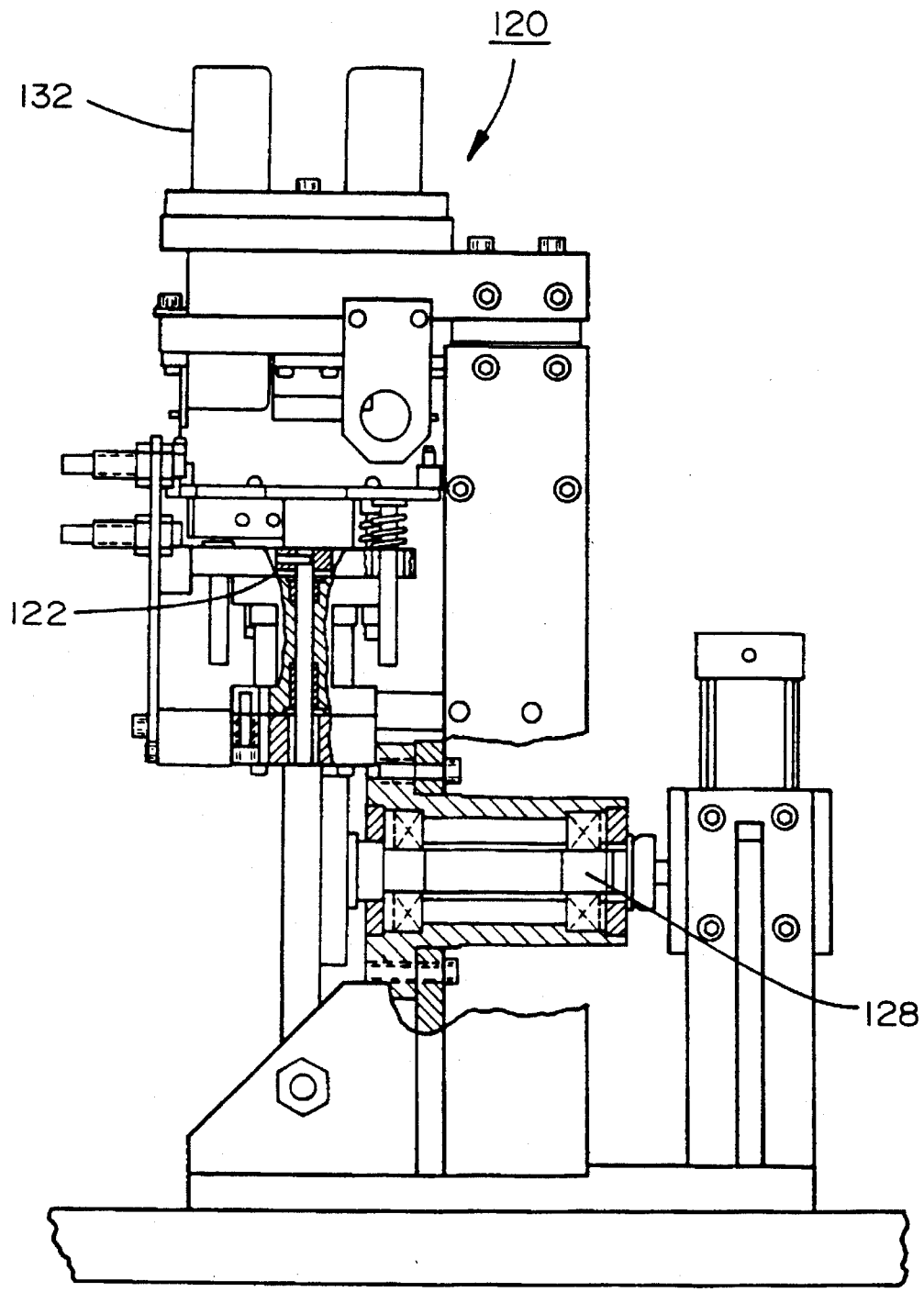
FIG. 14 illustrates a side elevational view of the cover-applying device of FIG. 13.

Upon any desired visual inspection having been completed, the rotary turret or turntable 10 is indexed to the this workstation, shown in FIGS. 13 to 15, which provides for the pivot arm structure 126 gripping a flat paper cover 150 in the vertical position of operation from a supply of covers, and positioning the cover in juxtaposition over the needle and suture-filled tray 148 mounted on its platform 42 of tool nest 16. Thereafter, the pressing die 123 on the pivot arm 122, in the horizontal is advanced towards the cover and underlying tray 148 subsequent to being pivoted into the horizontal position along arrow C, and implements a pressing action forming the latching tabs 156 in the cover, as shown in FIG. 22 of the drawing, and described hereinbefore, while concurrently punching out a small portion 168 of the cover 150 to form a product-identifying label which is pushed into the recessed area 162 of the tray to be permanently positioned therein so that, upon detaching of the cover 150 from tray 148 to gain access to the tray contents, the separated portion remaining in the tray provides suitable product-identifying legends.

The specific raised die surfaces, which are clearly shown in the drawings, are correlated with the particular recesses and cutouts provided in the tray 148, as is illustrated in FIG. 21.

Operation of Cover Removal Workstation (8)

After the cover 150 has been applied and fastened to the tray 148 as described, the now filled and completed suture package, as shown in FIG. 22, is indexed forwardly by the rotary turret 10 to workstation (8), as illustrated in FIGS. 16 to 18, in which pivotable grippers 172 on frame 174, in the horizontal position of pivot arm 173, are actuated to engage the sides of the suture package, and then retract and lift the suture package off the support platform 42 on which it has been mounted during the operation of the machine. Thereafter, the suture package is pivoted upwardly by swinging the pivot arm 173 upwardly along the direction of arrow D, so as to be in an alignment with and located below the bottom of chute 180, and then pushed upwardly by means of a ram 182 to disengage from the grippers and to become the lowermost component of a stack of suture packages in the chute 180. The lip 184 prevents the packages to fall down out of the chute, and which packages may then be optionally subsequently subjected to further processing as desired; for example, such as to sterilizing and/or further overwrap packaging, or the like.

During this particular operating cycle of the machine for the production of a finished suture package, as the package is advanced from workstation to workstation, at each indexing step during the rotation of the rotary turret 10, a subsequent suture package is produced by similar sequentially following manufacturing steps, thereby providing for a continuous automated suture package production sequence.

The foregoing indexing motions of the rotary turret 10 which are implemented in order to produce each completed suture package are correlated with each other through the program-controlled operation of the machine such that the dwelling-time periods for the tray and/or package at each the respective workstations is computed to allow sufficient time for the preceding step to allow been completed at the preceding workstation or workstations. This will enable a smooth and continuous flow of product from the automated packaging machine and provide for high-speed and efficient manufacturing cycles.

Although the invention has been described herein in connection with an automated packaging machine incorporating a rotary turret, quite apparently the machine may also be directed to an arrangement of linearly spaced workstations for a continuous packaging installation.

While there has been shown and described what are considered to be preferred embodiments of the invention, it will, of course, be understood that various modifications and changes in form or detail could readily be made without departing from the spirit of the invention. It is, therefore, intended that the invention be not limited to the exact form and detail herein shown and described, nor to anything less than the whole of the invention herein disclosed as hereinafter claimed.

What is claimed is:

1. A method for the automated packaging of needles having attached sutures to form suture packages, including automatically winding said sutures into a peripheral channel of a tray and attaching a cover to said tray so as to constitute said suture package, including advancing in indexed motions said tray while being supported on a tool next to a plurality of sequential spaced workstations stationarily arranged along the path of advancing movement of said tool nest; said method comprising the steps of:

(a) mounting an empty said tray at a first said workstation on a support surface of said tool nest;

(b) inserting a plurality of needles and attached sutures into said tray at a second workstation such that said needles are fastened in said tray in a predetermined array and said attached sutures include portions depending downwardly and outwardly from said tray;

(c) gathering said depending suture portions at a third workstation into a bundled strand and imparting axial tension thereto; rotating said support surface and mounted tray about an axis extending normal to the plane of said support surface and tray; and operatively in conjunction with gathering said suture, winding said bundled strand of depending suture portions into said peripheral tray channel;

(d) applying a cover to said tray at a fourth workstation to form said suture package containing said needles and attached wound sutures; and imparting pressure to said cover to form latching structure in said cover fastening said cover to said tray and concurrently severing a portion of the cover to form a label which is permanently attached to said tray;

(e) disengaging said completed suture package at a fifth workstation from said support surface on said tool nest.

2. An automated packaging method as claimed in claim 1, wherein at said second workstation a plurality of needles and attached sutures are received from a supply source, and including successively inserting said needles onto predetermined needle-clamping locations in said tray to form said array of needles and attached sutures.

3. An automated packaging method as claimed in claim 2, wherein an angular displacement from a vertical orientation is imparted to said support surface mounting said tray at said second workstation within the plane of said support surface to facilitate insertion of said needles into said tray to form said array.

4. An automated packaging method as claimed in claim 3, wherein said angular displacement rotates said support surface and tray through a tilting angle within the range of about 0° to 30° relative to a vertical axis.

5. An automated packaging method as claimed in claim 4, wherein said angular displacement subtends an angle of about 16° with the vertical axis.

6. An automated packaging method as claimed in claim 3, wherein said at least one tool nest defines an axis of rotation for enabling said angular displacement and rotational movement at, respectively, said second and third workstations.

7. An automated packaging method as claimed in claim 6, wherein at said second workstation said support surface is biased into said angularly oriented displacement during the insertion of said needles into said tray.

8. An automated packaging method as claimed in claim 2, wherein said supporting surface and tray are incrementally vertically shifted on said tool nest so as to correlate the successive insertion of said needles with said predetermined needle-clamping locations in said tray to form said needle array.

9. An automated packaging method as claimed in claim 8, comprising grippingly engaging and conveying a specified quantity of needles in successive sequence into said tray in synchronism with the incremental vertical displacement of said support surface and tray on said tool nest.

10. An automated packaging method as claimed in claim 9, wherein said incremental vertical displacement comprises shifting said support surface and tray in a direction normal to the direction of the indexed advance of said tool nest.

11. An automated packaging method as claimed in claim 8, wherein said tool nest comprises at least one housing; a cam plate being rotatable on an end of said housing facing said workstations, fastening said support surface to said cam plate so as to be secured against rotation relative to said cam plate, and providing said support surface with a vertically oriented platform mounting said tray in surface-contacting relationship thereon.

12. An automated packaging method as claimed in claim 11, wherein slide guide means interconnect said cam plate and said platform for implementing the vertical incremental shifting of said support surface relative to said cam plate during successive inserting of said needles and attached sutures into said tray.

13. An automated packaging method as claimed in claim 11, wherein the peripheral configurations of said cam plate and of said support surface generally conform with the external shape and are dimensioned larger than the size of said tray.

14. An automated packaging method as claimed in claim 1, wherein said support surface mounting said tray includes a plurality of projecting guide pins engageable in apertures formed in said tray for simultaneously positioning and securing said tray in a predetermined registered orientation on said support surface.

15. An automated packaging method as claimed in claim 11, wherein said depending suture portions at said third workstation are gathered by vacuum-generating means tensioning said suture portions into bundled strands.

16. An automated packaging method as claimed in claim 15, wherein said vacuum-generating means comprises a housing arranged below said supporting surface for said tray, a generally vertical slot in the interior of said housing for receiving said depending suture portions, comprising imparting to said housing interior a subatmospheric pressure for causing said depending suture portions to be tensioned within said slot and collected into said bundled strands.

17. An automated packaging method as claimed in claim 16, wherein said supporting surface and said tray are rotated about an axis extending perpendicular to the plane of said tray at said third workstation; for cooperatively winding said suture portions into said tray channel during rotation of said tray.

18. An automated packaging method as claimed in claim 17, wherein arm means comprising structure contacting said tensioned suture portions is pivoted for biasing said suture portions into an orientation facilitating winding of said suture portions into the tray channel.

19. An automated packaging method as claimed in claim 17, wherein a stylus arrangement operatively contacts said tensioned and bundled suture strands guiding said strands into said tray channel to facilitate winding of said sutures into said tray during rotation of said tray.

20. An automated packaging method as claimed in claim 19, wherein said stylus arrangement comprises stylus legs contacting said sutures, a piston rod mounting said stylus fingers at one end for axial movement, a stationary piston cylinder mounting said piston rod for reciprocatory motion therein to enable said stylus legs to engage into and follow said tray channel during rotation of said tray.

21. An automated packaging method as claimed in claim 20, wherein cam follower means are mounted on said piston rod proximate said stylus finger, comprising contacting a peripheral camming surface on said cam plate by said cam follower means responsive to axial pressure being exerted against said piston rod by pressurized air in said piston cylinder.

22. An automated packaging method as claimed in claim 21, wherein said cam follower means comprises cam rollers articulated on said piston rod.

23. An automated packaging method as claimed in claim 20, wherein said tray includes a plurality of resilient cantilevered fingers extending over said peripheral channel for protectively maintaining the sutures in said channel, said stylus legs engaging beneath successive of said fingers for raising said fingers during rotation of said tray and support surface and continually guidingly therebeneath and biasing said bundle of sutures into and towards the bottom of said tray channel.

24. An automated packaging machine as claimed in claim 17, wherein said tray is contacted by restrain means operatively connected to drive means during rotation of said tray so as to inhibit said tray on said support surface from being displaced therefrom.

25. An automated packaging method as claimed in claim 1, wherein winding said depending suture portions at said third workstation comprises rotating said supporting surface and tray about an axis extending perpendicular to the plane of said tray.

26. An automated packaging method as claimed in claim 25, wherein said tool nest is rotated about said axis, and said supporting surface is concurrently rotated by shaft having a pair of rotatable cam rollers mounted thereon; and a stationary camming surface extending between said collective workstations being contacted by said cam rollers for normally maintaining said at least one tool nest in a vertically-oriented upright position.

27. An automated packaging method as claimed in claim 26, wherein said rotation is implemented by a driving motor; a drive pulley driven by said driving motor; a driven pulley rotatably journaled so as to at least partially extend into a cutout formed in said camming surface at said third workstation; a drive belt interconnecting said pulleys, and said cam rollers being operatively engageable with said driven pulley for rotating said shaft responsive to rotational movement being imparted to said driven pulley.

28. An automated packaging method as claimed in claim 27, wherein said driven pulley includes a slot, said cam rollers and contiguous end of said shaft being centered in said slot upon said tool nest being indexed to said third workstation, whereby rotation of said driven pulley imparts rotational movement to said cam rollers engaged in said slot about the longitudinal axis of said shaft causing said shaft to rotate said supporting surface so as to wind said sutures into said tray.

29. An automated packaging method as claimed in claim 27, wherein said driving motor comprises a servomotor.

30. An automated packaging method as claimed in claim 27, wherein said pulleys comprise sprocket wheels and said drive belt comprises a sprocket belt.

31. An automated packaging method as claimed in claim 1, wherein at said cover-applying workstation, a pivotable arm having grippers successively obtains individual covers from a supply of covers, pivoting said grippers into alignment with said tray on said support surface and extending said grippers to position said cover on said tray such that the guide pins extend through openings in said cover, releasing said cover and withdrawing said grippers.

32. An automated packaging method as claimed in claim 31, wherein said tray includes first and second planar areas, pressure-imparting means comprising a die separating said applied cover into two portions, a first of said portions being applied to said first planar area and a second of said portions being affixed to said second planar area.

33. An automated packaging method as claimed in claim 32, wherein said pressure-imparting die means effectuates a severing action forming tabs in said cover for latching engaging cooperating latching elements on said tray upon the application of said cover thereto.

34. An automated packaging method as claimed in claim 1, wherein said tray is a flat tray having a plurality of needles and attached sutures mounted therein, the sutures extending from the needles being wound into a peripheral channel formed by upstanding walls of said tray encompassing a central surface area of said tray, said tray including a plurality of latching elements and an upstanding wall structure defining a second planar surface area within the confines of said central surface area, said cover is a generally flat member coextensive with the dimensions of said tray and supported on the upper ends of the walls of said peripheral channel, said upstanding wall structure defining said second planar surface area; said cover-applying method comprising the steps of:

(a) pressing said cover against said tray, said pressure imparting steps including:
  (1) pressing a die having a surface for pressing the cover against the upper edges of the tray channel walls;
  (2) causing protruding means on said pressing means to form a plurality of latching tabs extending from said cover and causing each said tab to be latchingly engaged with a respective one of said latching elements on said tray;
  (3) and causing severing means on said pressure imparting die to separate a portion of said cover substantially coextensive with said second planar surface area and positioning said severed cover portion within the confines of said upstanding wall structure of said tray defining said second planar surface area.

35. An automated packaging method as claimed in claim 34, wherein said severing means comprises a raised surface for depressing said separated cover portion into recessed surface contact with the second planar surface of said tray so as to enable said severed cover portion to remain attached to said tray upon subsequent detachment of the remaining cover portion from said tray.

36. An automated packaging method as claimed in claim 34, wherein said latching elements each comprise walls forming a recess having a central opening therein, said protruding means on said pressure imparting means including knife edges partially severing said cover to form said latching tabs and to concurrently configure said tabs into V-shapes each extendable through respectively one of said openings into latching engagement in respective of said recesses.

37. An automated packaging method as claimed in claim 34, wherein said severing means for separating said cover portion includes peripheral edge surfaces slidingly engageable with the interior surfaces of the wall structure defining said second planar surface area of the tray so as to form a cutting edge for separating said cover portion from the remaining cover.

38. An automated packaging method as claimed in claim 34, wherein said separated cover portion forms a product-identifying label permanently fastened to said tray.

39. An automated packaging method as claimed in claim 1, wherein a tray-detecting workstation is located stationarily proximate said tool nest intermediate said first and second workstations, said tray-detecting workstation including a sensor for detecting the presence of a tray on said support surface.

40. An automated packaging method as claimed in claim 1, wherein a needle-detecting workstation is located between said second and third workstations, said needle-detecting workstation comprising a plurality of sensors reciprocable towards and away from said needle-containing tray to enable verification of the presence and positioning of an appropriate quantity of needles in said tray.

41. An automated packaging method as claimed in claim 1, wherein an inspection workstation is located between said third and fourth workstations to facilitate visual inspection of the contents of the tray.

42. An automated packaging method as claimed in claim 41, wherein said suture package is disengaged from the support surface at said fifth workstation by a pivotable gripper arrangement conveying said suture package to a storage chute.

43. An automated packaging method as claimed in claim 1, wherein a plurality of said tool nests having said support surfaces for mounting trays are arranged spaced about the circumference of an indexing rotary turret.

44. An automated packaging method as claimed in claim 43, wherein the number of support surfaces is selected to be commensurate with the number of workstations stationarily arranged about said rotary turret.

\* \* \* \* \*